United States Patent
Tegels et al.

(10) Patent No.: US 9,743,920 B2
(45) Date of Patent: Aug. 29, 2017

(54) FLEXIBLE TAMPING MEMBER

(75) Inventors: Zachary J. Tegels, Minneapolis, MN (US); Steven Willard, Bloomington, MN (US); Russell D. Terwey, St. Michael, MN (US); Troy T. White, Maple Grove, MN (US)

(73) Assignee: TERUMO PUERTO RICO, L.L.C., Caguas, PR (US)

( * ) Notice: Subject to any disclaimer, the term of this patent is extended or adjusted under 35 U.S.C. 154(b) by 141 days.

(21) Appl. No.: 13/589,912

(22) Filed: Aug. 20, 2012

(65) Prior Publication Data
US 2014/0052172 A1     Feb. 20, 2014

(51) Int. Cl.
| A61B 17/08 | (2006.01) |
| A61B 17/00 | (2006.01) |
| A61B 90/00 | (2016.01) |

(52) U.S. Cl.
CPC .......... *A61B 17/0057* (2013.01); *A61B 90/03* (2016.02); *A61B 2017/00637* (2013.01); *A61B 2017/00654* (2013.01); *A61B 2017/00858* (2013.01); *A61B 2017/00991* (2013.01); *A61B 2090/032* (2016.02)

(58) Field of Classification Search
CPC ...... A61B 17/0057; A61B 2017/00637; A61B 2017/00654; A61B 19/30
USPC ................. 606/213, 215, 216, 232
See application file for complete search history.

(56) References Cited

U.S. PATENT DOCUMENTS

| 5,711,909 A | 1/1998 | Gore et al. |
| 5,919,205 A | 7/1999 | Heimberger et al. |
| 6,045,569 A | 4/2000 | Kensey et al. |
| 6,090,130 A | 7/2000 | Nash et al. |
| 7,250,057 B2 | 7/2007 | Forsberg |
| 7,597,705 B2 | 10/2009 | Forsberg et al. |
| 7,618,436 B2 | 11/2009 | Forsberg |
| 7,749,248 B2 | 7/2010 | White et al. |
| 7,837,705 B2 | 11/2010 | White et al. |
| 7,931,670 B2 | 4/2011 | Fiehler et al. |
| 8,414,574 B2 | 4/2013 | Sugita |
| 2001/0012944 A1* | 8/2001 | Bicek ................ A61F 2/95 606/108 |

(Continued)

FOREIGN PATENT DOCUMENTS

| DE | 19636976 A1 | 3/1998 |
| DE | 102007025491 A1 | 12/2007 |

(Continued)

OTHER PUBLICATIONS

PCT International Search Report for International PCT No. PCT/US2013/051039, mailed Jan. 20, 2014 (6 pp.).

*Primary Examiner* — Ashley Fishback
(74) *Attorney, Agent, or Firm* — Buchanan Ingersoll & Rooney PC

(57) ABSTRACT

Methods and apparatus are disclosed for sealing a puncture or incision formed percutaneously in tissue separating two internal portions of the body of a living being with an anchor, a sealing plug and a filament connecting the anchor and sealing plug. The methods and apparatus provide for a compaction device or a tamping device that improves control of the amount of force exerted upon the sealing plug. Further, the compaction tube or tamping device can deform upon application of excessive compaction force, thereby reducing the possibility of damage to the sealing plug, anchor, or artery.

31 Claims, 25 Drawing Sheets

(56) References Cited

U.S. PATENT DOCUMENTS

| | | |
|---|---|---|
| 2003/0014092 A1 | 1/2003 | Neuhann |
| 2005/0267522 A1* | 12/2005 | Yassinzadeh et al. ........ 606/213 |
| 2006/0095018 A1 | 5/2006 | Pursley |
| 2007/0060847 A1* | 3/2007 | Leo .................... A61B 5/0084 |
| | | 600/587 |
| 2008/0082123 A1 | 4/2008 | Forsberg et al. |
| 2012/0245597 A1 | 9/2012 | Tegels |

FOREIGN PATENT DOCUMENTS

| | | | |
|---|---|---|---|
| EP | 1250900 A2 | 10/2002 | |
| IL | EP 2238901 A2 * | 10/2010 | ............... A61B 5/05 |

* cited by examiner

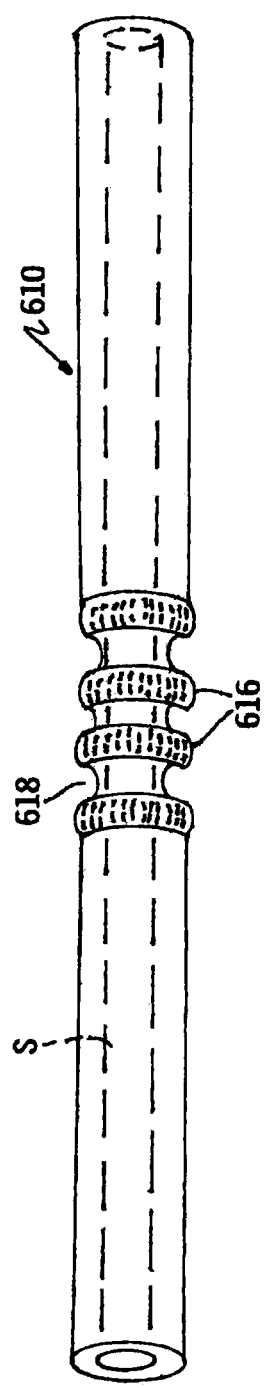

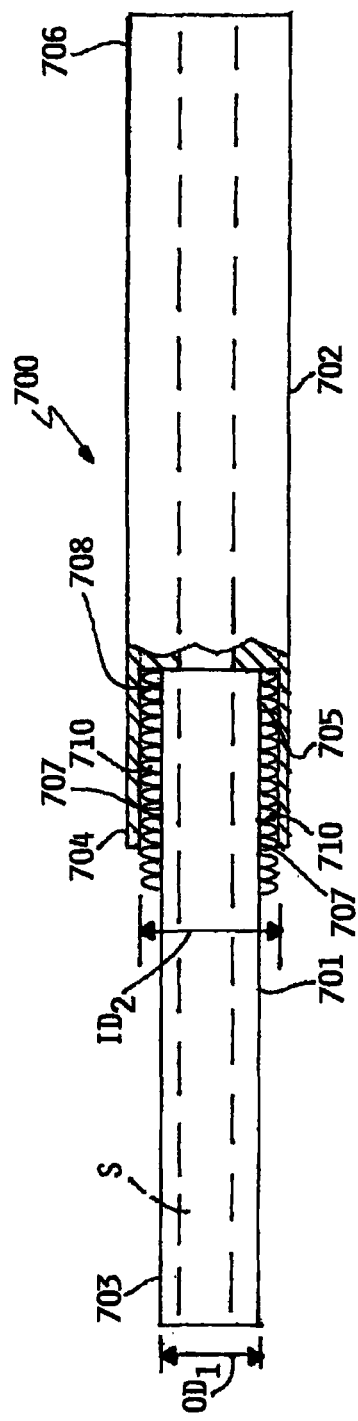
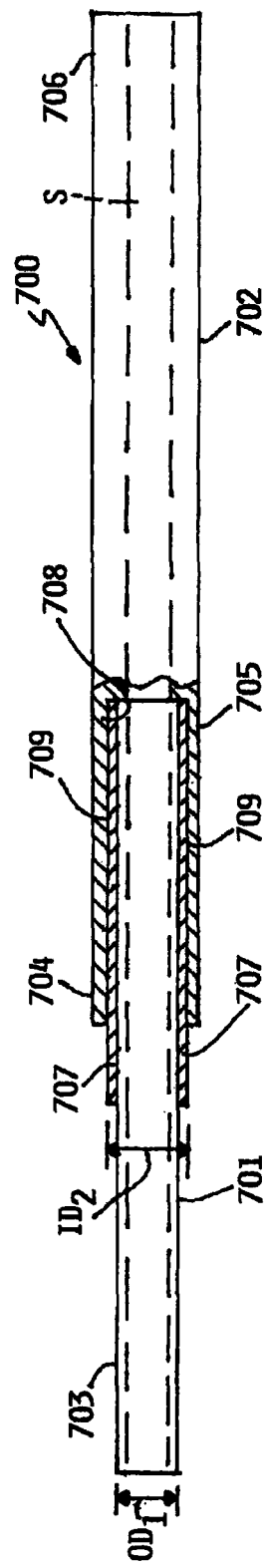

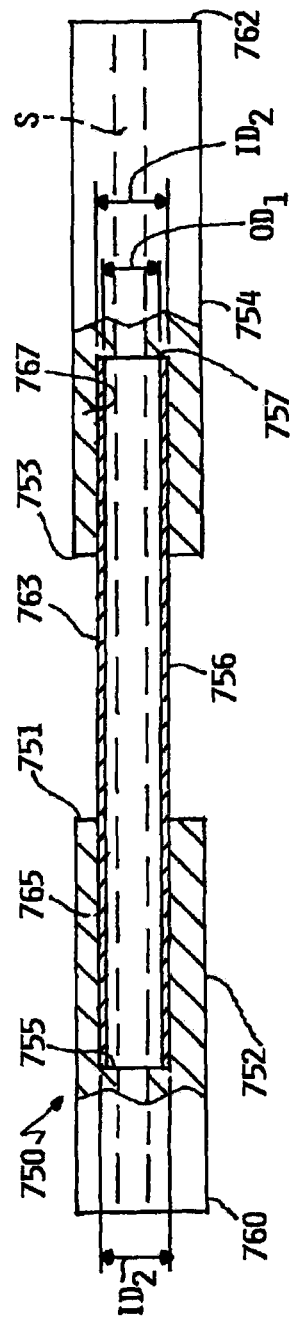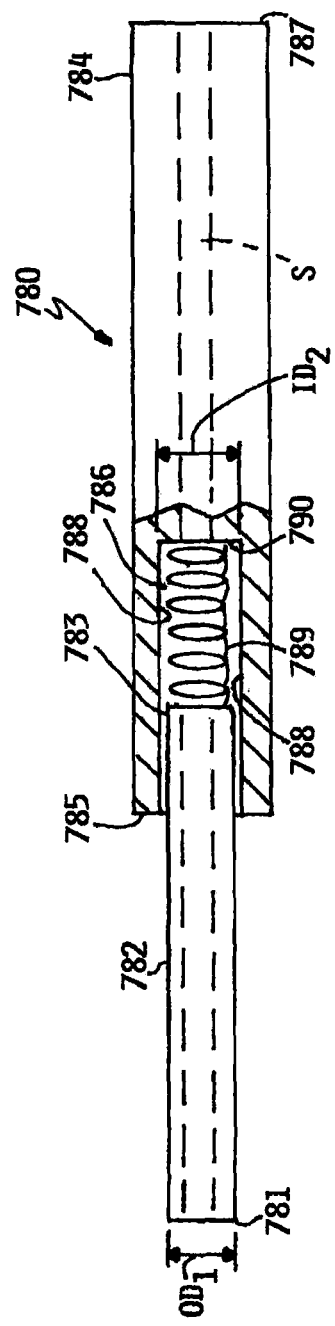
FIG. 23
FIG. 24

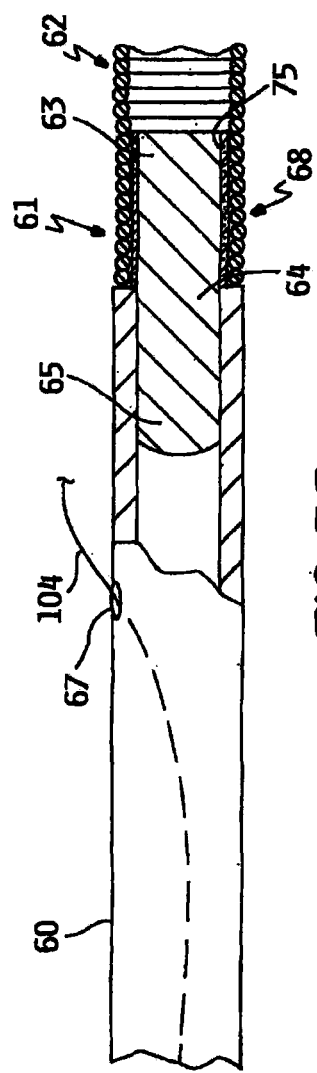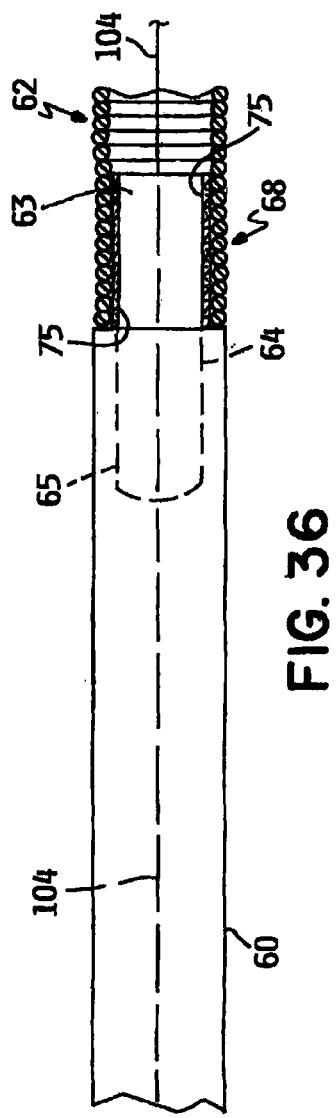

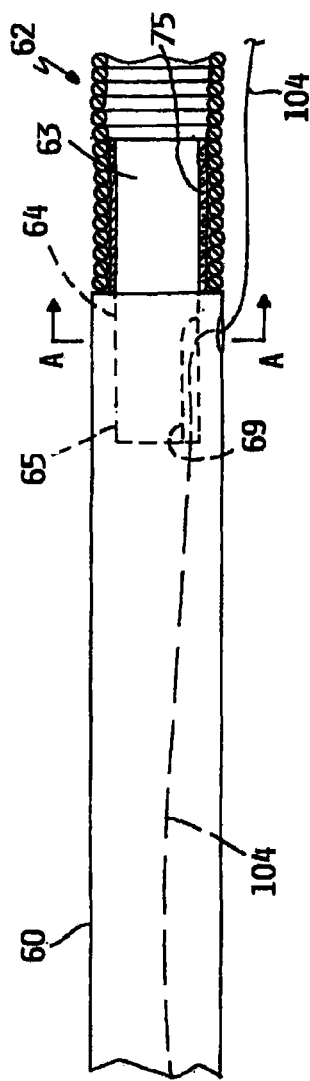
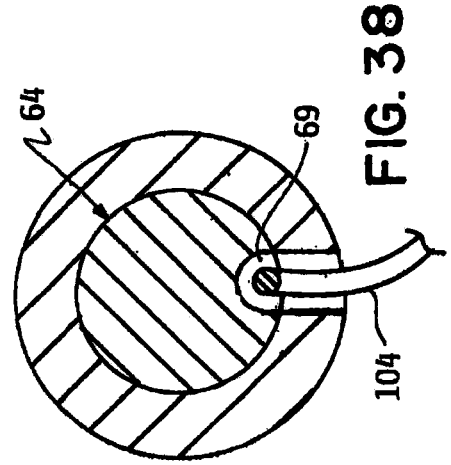

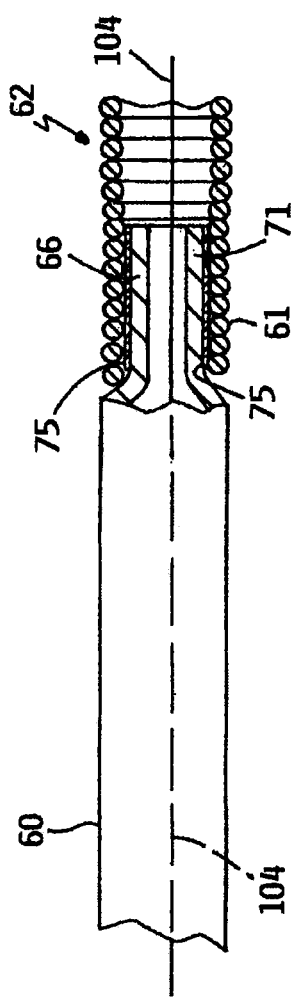
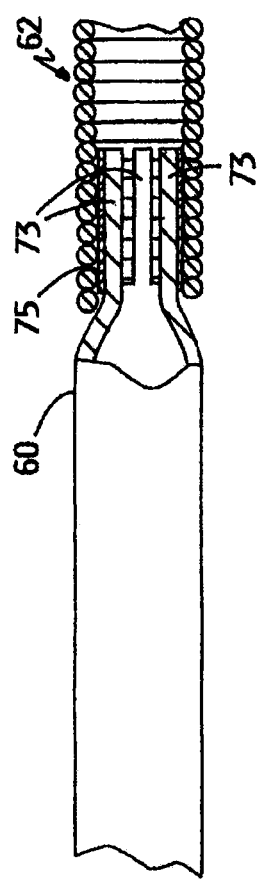
FIG. 40
FIG. 40A

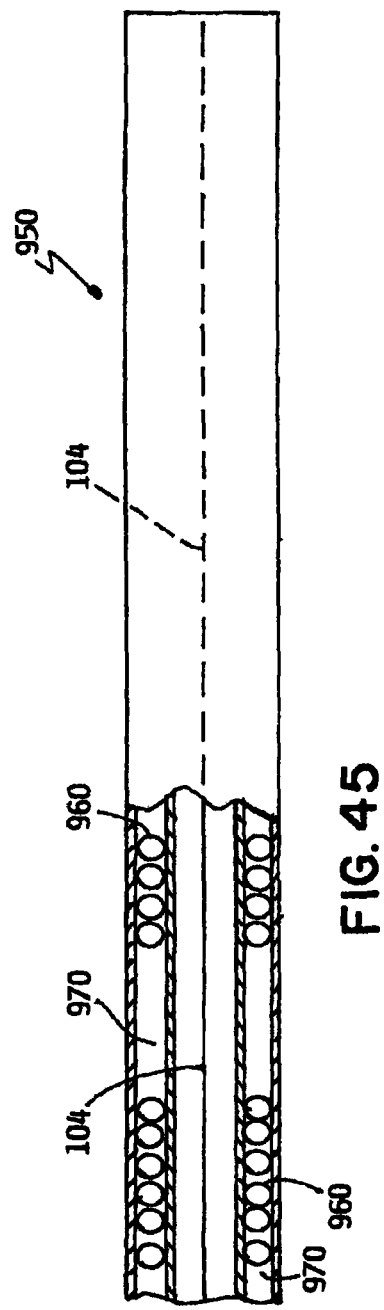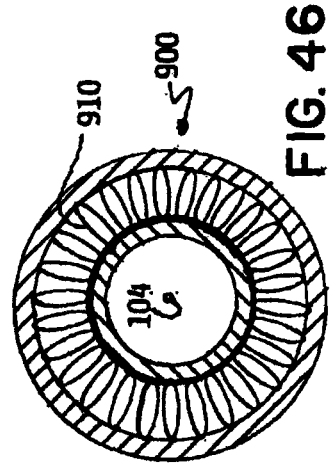

FLEXIBLE TAMPING MEMBER

FIELD OF THE DISCLOSURE

This disclosure relates generally to medical devices and more particularly to tools for sealing punctures or incisions in a tissue wall.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,045,569; 6,090,130; 7,597,705; 7,618,436, 7,749, 248; 7,837,705; 7,931,670, and related patents and patent applications, all of which are hereby incorporated by reference.

Typical closure tools or devices such as the ones described in the above-mentioned patents and patent applications place a sealing plug at the tissue puncture site. Successful deployment of the sealing plug requires that it be ejected from within a device sheath into the incision or puncture tract and tamped down to an outer surface of the tissue puncture using a tamping tube (also called a compaction tube). In a manually operated tool, the tamping procedure cannot commence until the device sheath (within which the tamping tube is located) has been removed so as to expose the tamping tube for manual grasping. The tamping tube is manually grasped and tamped against the sealing plug, setting the sealing plug within the incision or puncture tract, against an outer surface of the tissue puncture. In an automatic tamping system, the closure tool can have an automatic driving mechanism for automatically tamping the sealing plug within the incision or puncture tract toward the outer surface of the tissue puncture. The closure tool can have a tamping tube disposed adjacent to the sealing plug, such that the tamping tube is driven by the automatic driving mechanism to tamp the sealing plug into the desired placement.

Under certain conditions, the force used to tamp the sealing plug may not be controlled to the desired extent and the sealing plug may not be tamped into the desired placement; potentially, the sealing plug may be tamped too forcefully resulting in over-compaction of the sealing plug within the incision or puncture tract, or extension of the sealing plug into the artery lumen. Accordingly, there is a need for improving the mechanism for deployment of the sealing plug at the site of a tissue puncture and improving control of the amount of force exerted upon the sealing plug.

SUMMARY

In one of the many possible embodiments, the present disclosure provides a compaction device or a tamping device for tamping a sealing plug within an incision or puncture tract, towards the outer surface of a tissue puncture, where the compaction device is adapted to at least partially absorb excessive compaction force applied to the compaction device, and thus, to the sealing plug. It should be noted that the terms "compaction device" and "tamping device" are used interchangeably and refer to the same component of the tissue puncture closure tool. The term "compaction device" may refer to a "compaction tube" or other such similar device. In one aspect, the compaction device of the present disclosure can be used in a tissue puncture closure tool where the compaction device is manually grasped and used to tamp the sealing plug. Further, in another aspect, the compaction device can be used with a tissue puncture closure tool where the compaction device automatically tamps the sealing plug. The compaction devices described below can be used in a manual tamping system as well as in an automatic tamping system.

According to one aspect of the disclosure, the compaction device comprises a tubular member wherein at least one segment of the tubular member includes a structure that is designed to compress, collapse, buckle, or deform in some way, to absorb applied excessive compaction force. In some aspects of the disclosure, the compaction device comprises a tubular member wherein the tubular member includes a plurality of structures that are designed to compress, collapse, buckle, or deform in some way, to absorb applied excessive compaction force.

In one aspect of the disclosure, the compaction device comprises a tubular member and includes a plurality of pleats or accordion folds. In another aspect of the disclosure, the compaction device comprises a tubular member and includes a segment, or a plurality of segments, where the segment is a web or lattice. In yet another aspect of the disclosure, the compaction device comprises a tubular member and includes a segment, or a plurality of segments, where the segment(s) has some material of the compaction tube cut-out, leaving various shaped apertures in the segment(s) of the compaction device. The cut-outs can be arranged in a pattern in the wall of the compaction device, can circumscribe the compaction device and/or can be randomly arranged.

According to yet another aspect of the present disclosure, the compaction device can comprise a tubular member and can include at least one spring, wound wire, or coil in at least one segment of the compaction device, or at one of the ends of the compaction device. In yet another aspect of the disclosure, the compaction device can include at least two tubular members wherein one tubular member is engaged with the second tubular member. However, the at least two tubular members are immovably structurally stable relative one to another, until an applied excessive compaction force causes the at least two tubular members to slidingly engage with one another.

According to another aspect of the present disclosure, the compaction device can comprise a tubular member and can include a rigid segment and a more flexible, compressible, segment. The more flexible segment can include the tip of the compaction device tubular member. The tip of the compaction device tubular member can take on various shapes, such that the footprint of the tip provides a large surface area to use in tamping the sealing plug.

One skilled in the art would understand that the various aspects of the present disclosure described above can be combined and intermixed into various other arrangements and combinations, to achieve the desired flexibility, compressibility, buckling, or deformability, desired in the compaction device.

In another aspect of the disclosure, a compaction device that is coilable is disclosed. The coilable compaction device can be coiled within a handle of a tissue puncture closure tool and, when extended longitudinally, the compaction device has sufficient column strength to tamp the sealing plug into place. Further, the compaction device can deform to absorb excessive compaction force applied to the compaction device.

In yet another aspect of the disclosure, a compaction device comprises a rack as well as a compaction tubular member. The interface between the rack and the tubular member can be direct or, alternatively, the interface mechanism can engage the tubular member and the rack, wherein the interface mechanism can be a connector, for example, a spacer, a core wire, press-fits, and the like. The rack is utilized to automatically urge a tubular member toward the sealing plug, to tamp the sealing plug into place. The rack can be a coilable rack or a non-coilable linear rack, and can be used with a compaction tubular member, including the tubular members described above. Additionally, the interface between the rack and the compaction tubular member can be designed such that excessive compaction force is at least partially absorbed at the interface between the rack and the compaction tubular member. The rack can be considered as part of the compaction device, along with the compaction tubular member.

According to another aspect of the disclosure, there is disclosed a tissue puncture closure tool for partial insertion into and sealing of an internal tissue wall puncture. The tissue closure tool includes a filament extending from a first end of the closure tool to a second end of the closure tool, an anchor for insertion through the tissue wall puncture attached to the filament at the second end of the closure tool, a sealing plug slidingly attached to the filament adjacent to the anchor, and a compaction device proximally adjacent to the sealing plug for advancing the sealing plug toward the anchor. The compaction device can be coilable, or alternatively, not coilable. The tissue puncture closure tool may include a spool or a track at the first end, such that a portion of the coilable compaction device coiled on the spool or in the track is flexible, and a portion of the compaction device adjacent to the sealing plug has the column strength to tamp the sealing plug into place. The compaction device can be deformable to at least partially absorb excessive compaction force exerted on the compaction device, and thus, the sealing plug.

The above summary of the various representative embodiments is not intended to describe each illustrated embodiment or every implementation of the disclosure. Rather, the embodiments are chosen and described to that others skilled in the art may appreciate and understand the principles and practices of the disclosure. The figures in the detailed description that follows more particularly exemplify these embodiments.

BRIEF DESCRIPTION OF THE DRAWINGS

These as well as other objects and advantages of this disclosure will be more completely understood and appreciated by referring to the following more detailed description of the various example embodiments of the disclosure in conjunction with the accompanying drawings of which:

FIG. 18A is a perspective side view of a compaction device tubular member according to one embodiment;

FIG. 21 is a top planar view of a compaction device according to one embodiment;

FIG. 22 is a side cut-away view of a compaction device according to one embodiment;

FIG. 23 is a side cut-away view of a compaction device according to one embodiment;

FIG. 24 is a side cut-away view of a compaction device according to one embodiment;

FIG. 35 is a side partial cut-away view of a compaction tube, coilable rack and connector/core wire according to one embodiment;

FIG. 36 is a side partial cut-away view of a compaction tube, coilable rack and connector/spacer according to one embodiment;

FIG. 37 is a side partial cut-away view of a compaction tube, coilable rack and connector/spacer with a recess in the connector/spacer according to one embodiment;

FIG. 38 is a cross-sectional view of a connector/spacer with a recess, taken along A-A for FIG. 37 according to one embodiment;

FIG. 40 is a side partial cut-away view of a tipped compaction tube, and coilable rack, according to one embodiment;

FIG. 40A is a side partial cut-away view of a prong-ended compaction tube, and coilable rack, according to one embodiment;

FIG. 45 is a side view of a coilable compaction device according to one embodiment, and FIG. 46 is a cross-sectional view of a coilable compaction device according to one embodiment, taken along line A-A of FIG. 43.

Figure 1:
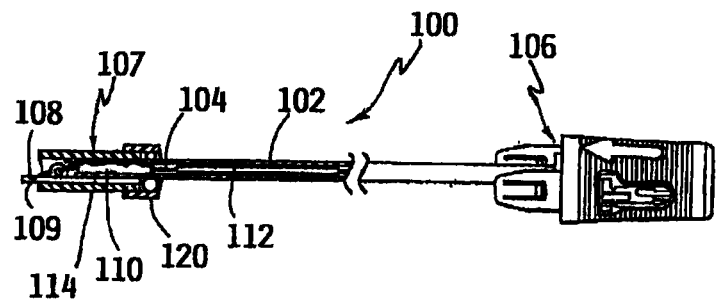
FIG. 1 is a side view, partly in section, of an internal tissue puncture closure tool.

While the disclosure embodiments are amenable to various modifications and alternative forms, specifics thereof have been shown by way of example in the drawings and will be described in detail. It should be understood, however, that the intention is not to limit the disclosure to the particular embodiments described. On the contrary, the disclosure is to cover all modifications, equivalents, and alternatives.

DETAILED DESCRIPTION

As mentioned above, vascular procedures are conducted throughout the world and require access to an artery through a puncture. Most often, the artery is a femoral artery. To close the puncture following completion of the procedure, many times a closure tool is used to sandwich the puncture between an anchor and a sealing plug. The closure tool can also be used to close other tissue punctures, punctures other than a puncture accessing a blood vessel, such as, for example, a puncture accessing a body cavity. However, sometimes the sealing plug is not properly seated against an exterior situs of the tissue puncture, for example, of the arteriotomy. If the plug does not seat against the arteriotomy, there is a potential for prolonged bleeding. The present disclosure describes methods and apparatus to reduce or eliminate misplacement of the sealing plug with a compacting device and/or to apply a more consistent compaction force to the sealing plug, without applying excessive compaction force. While the vascular instruments shown and described below include insertion sheaths and puncture sealing devices, the application of principles described herein are not limited to the specific devices shown. The principles described herein may be used with any vascular closure or similar device.

As used in this specification and the appended claims, the term "tamp" or "tamping" is used broadly to mean packing down by one or a succession of blows or taps or smooth, steady pressure. A "tamping tube" is used broadly to mean any elongated device or series of devices, including any intermediate components, used alone or in combination to tamp something else directly or indirectly. The term "compaction tube" is used interchangeably with the term "tamping tube". "Engage" and "engageable" are also used broadly to mean interlock, mesh, or contact between two devices. A "spool" is a cylinder or other device on which something else is at least partially wound. A "lumen" refers to any open space or cavity in a bodily organ or device, especially in a blood vessel. "Automatic" means no action or intervention is required by a human operator. "Transduce" means to convert a force or other input energy in one form into output energy or forces of another form or direction. "Gradually" means advancing or progressing by regular or continuous degrees, or absent any abrupt changes. "Sudden" refers to a rapid, abrupt, or quick change. The words "including" and "having," as used in the specification, including the claims, have the same meaning as the word "comprising."

Referring now to the drawings, and in particular to FIGS. 1-4, a vascular puncture closure tool 100 is shown according to the prior art. The vascular puncture closure tool 100 includes a carrier tube 102 with a filament or suture 104 extending at least partially therethrough. The closure tool 100 also includes a first or proximal end 106 and a second or distal end 107. External to a second or distal end 107 of the carrier tube 102 is an anchor 108. The anchor can be an elongated, stiff, low profile member including an eye 109 formed at the middle. The anchor 108 is typically made of a biologically resorbable polymer.

The suture 104 is threaded through the anchor 108 and back to a sealing pad; for example, a collagen pad 110. The collagen pad 110 can be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure tool 100 is properly placed and the anchor 108 deployed (see FIG. 4).

The carrier tube 102 typically includes a compaction device, tamping tube or compaction tube 112, disposed therein. The compaction tube 112 is slidingly mounted on the suture 104 and can be used by an operator to tamp the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 can be temporarily held in place flush with the carrier tube 102 by a bypass tube 114 disposed over the distal end 107 of the carrier tube 102.

Figure 2:
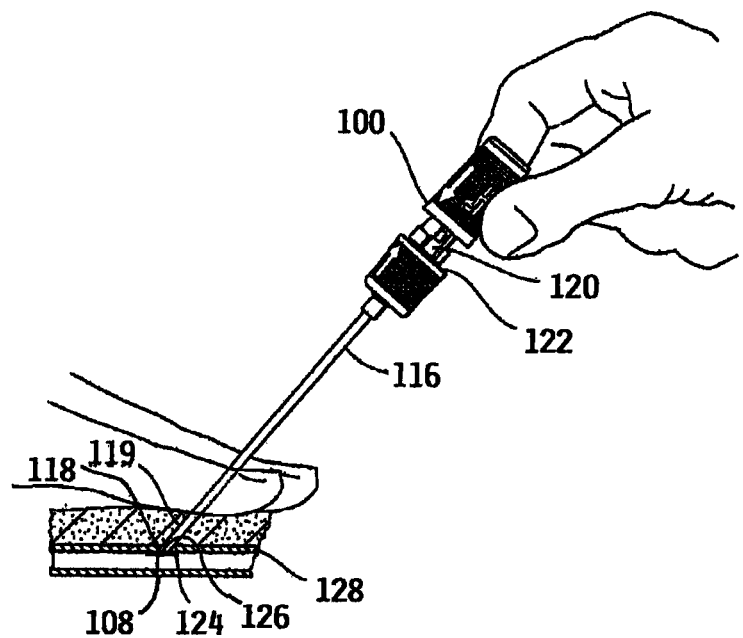
FIG. 2 is a side view of the tissue puncture closure tool of FIG. 1 inserted through an insertion sheath and engaged with an artery, the artery shown in section.
Figure 3:
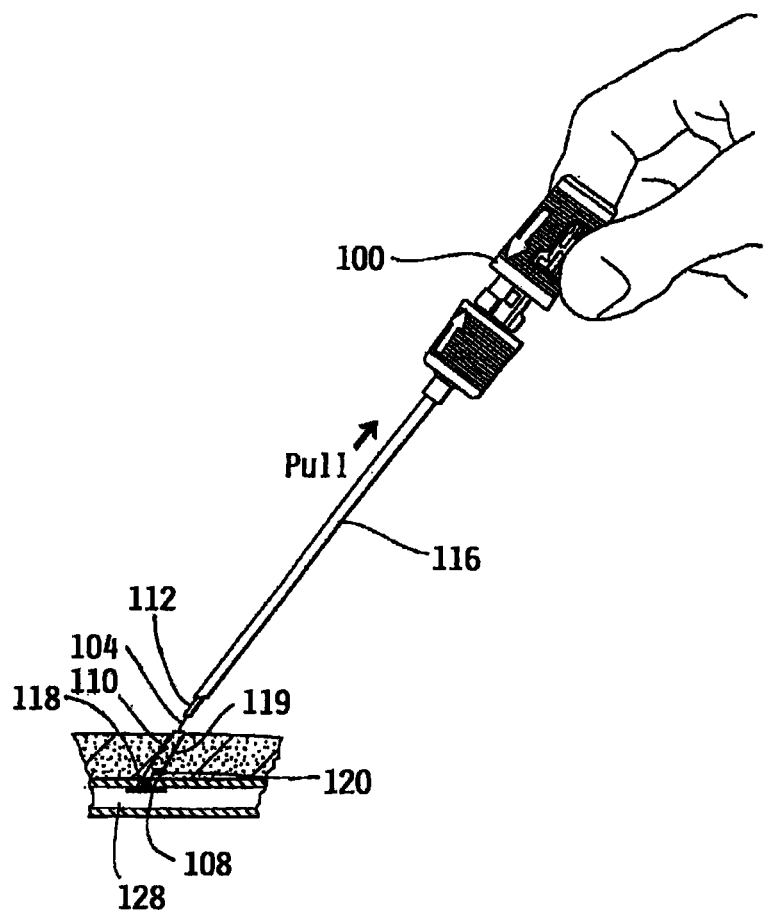
FIG. 3 is a side view of the tissue puncture closure tool, insertion sheath, and artery of FIG. 2, wherein the tissue closure tool and insertion sheath are being withdrawn from the artery to deploy a sealing plug.
Figure 4:
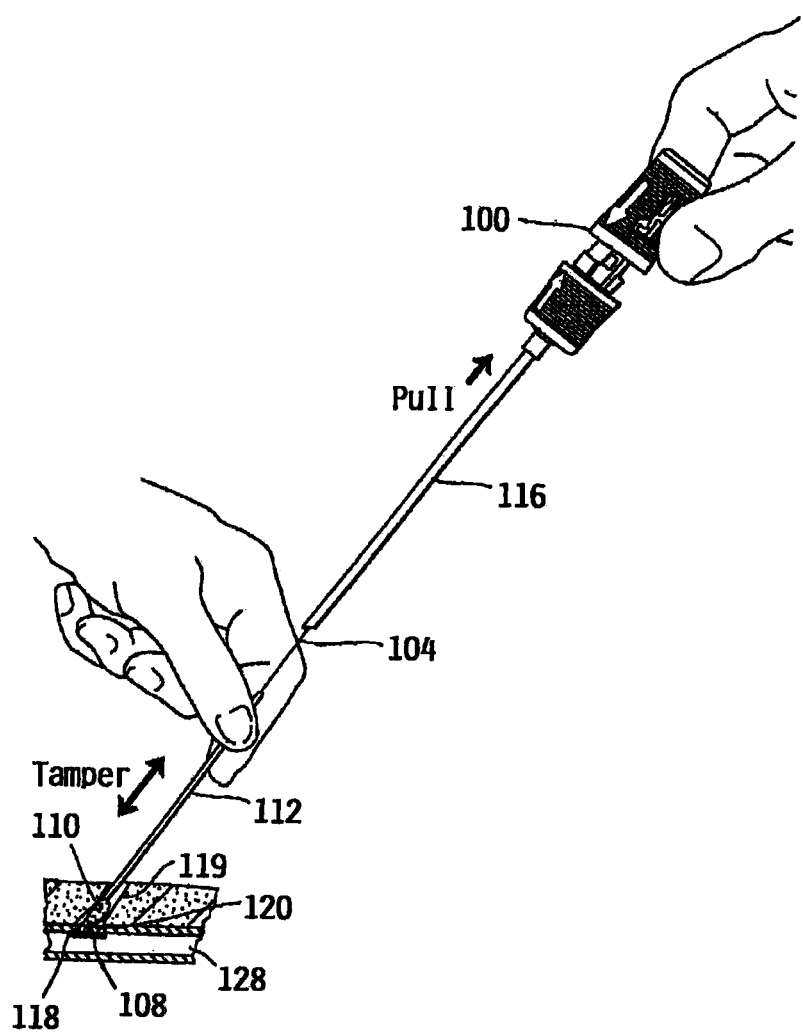
FIG. 4 is a side view of the tissue puncture closure tool, insertion sheath, and artery shown in FIG. 3 with a compaction device fully exposed and being used to tamp the sealing plug.

The flush arrangement of the anchor 108 and carrier tube 102 allows the anchor 108 to be inserted into an insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 from passing through an internal passage of the insertion sheath 116. Therefore, as the puncture closure tool 100 is inserted into the insertion sheath 116, the oversized head 120 bears against a surface 122 of the insertion sheath 116. Further insertion of the puncture closure tool 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114 as the insertion sheath 116 continues to limit anchor 108 movement.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 thereof. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure tool 100 and the insertion sheath 116 can be withdrawn together, forcing the collagen pad 110 through the tip of the carrier tube 102 and depositing it in the incision tract 119. The compaction tube 112 is also exposed. With the compaction tube 112 fully exposed as shown in FIG. 4, the compaction tube 112 can be manually grasped, the collagen pad 110 can be manually tamped, and the anchor 108 and collagen pad 110 can be cinched together and held in place with the self-tightening slip-knot on the suture 104. Thus, the tissue puncture is sandwiched between the anchor 108 and the collagen pad 110, thereby sealing the tissue puncture 118. The suture 104 can then be cut and the incision tract 119 can be closed. The suture 104, anchor 108, and collagen pad 110 are generally made of resorbable materials and therefore can remain in place while the puncture 118 heals.

Figure 5:
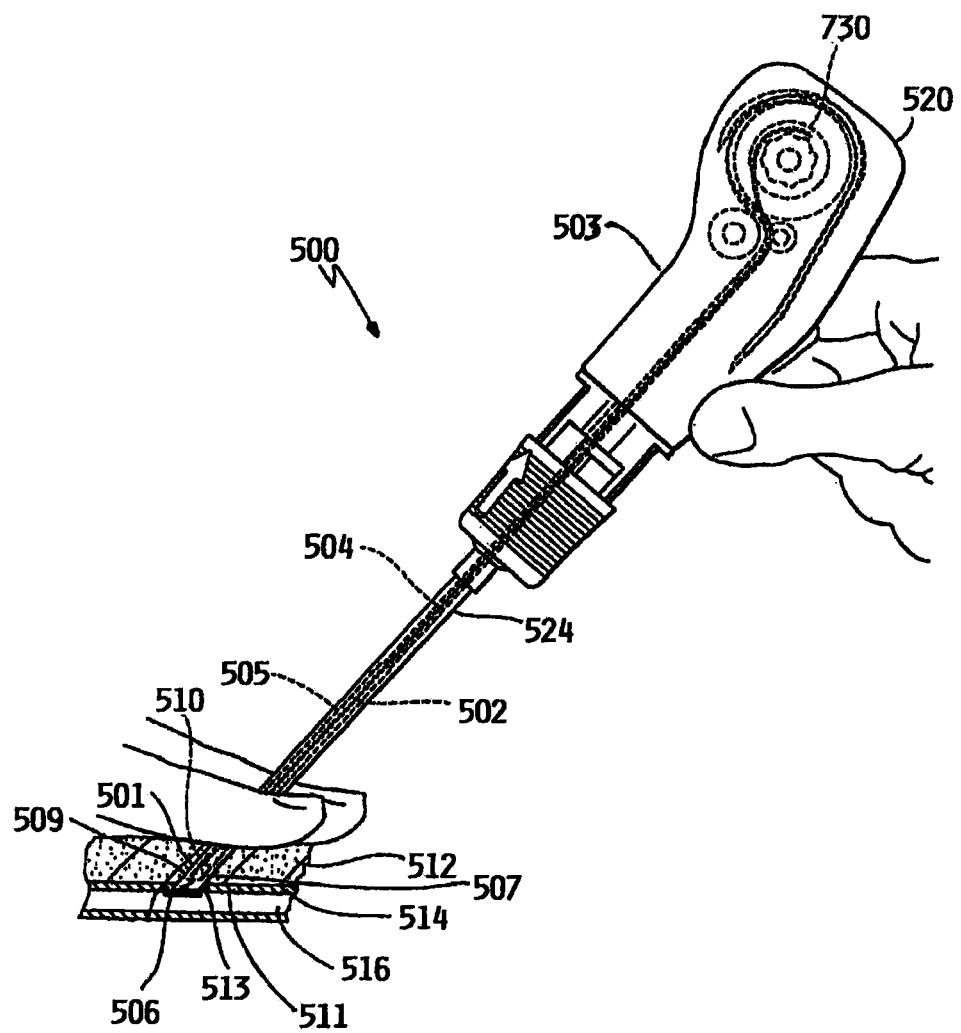
FIG. 5 is a side view of a tissue puncture closure tool with an automatic compaction mechanism shown engaged with an artery.
Figure 6:
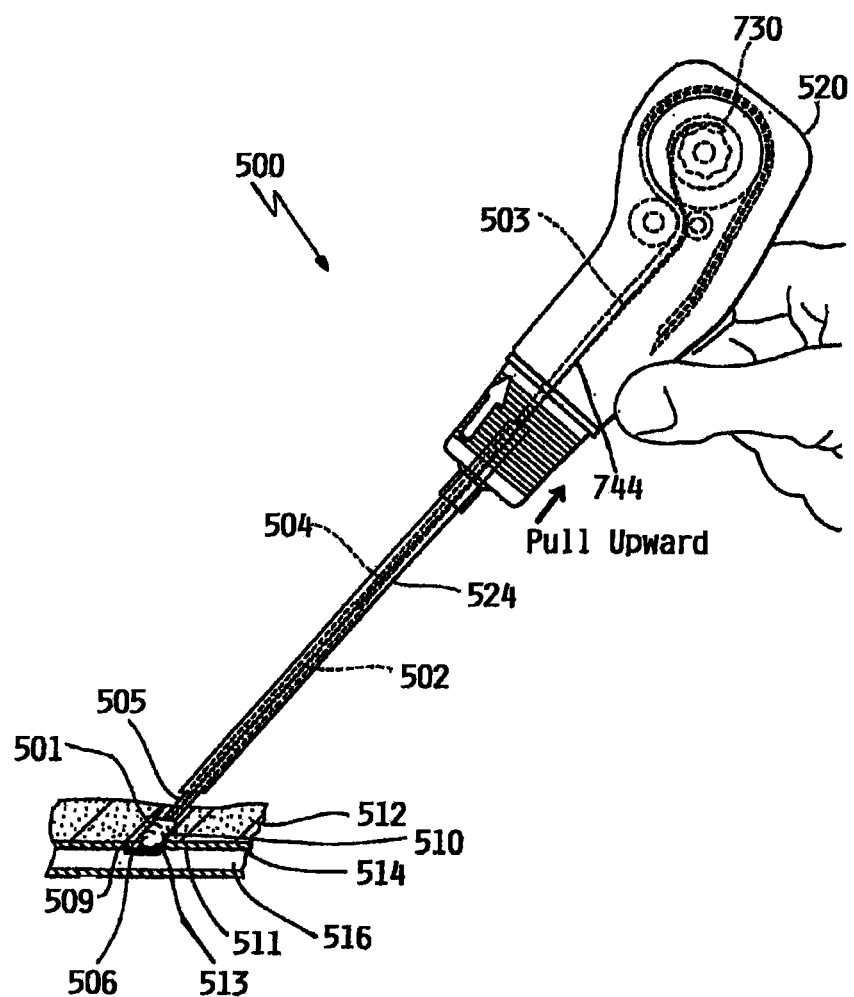
FIG. 6 is a side view of the tissue puncture closure tool of FIG. 5 being withdrawn from an artery.

Referring to FIGS. 5 and 6, there is shown another tissue puncture closure tool. The tissue puncture closure tool 500 includes a first or proximal end 503 and a second or distal end 507. A carrier tube 504 extends from the proximal end 503 to the distal end 507 and includes an outlet 513. The carrier tube 504 may be made of plastic or other material and is designed for insertion through a sheath 524 which is designed for insertion through a percutaneous incision 501 in a tissue layer 512 and into a lumen 516. As shown in FIG. 5, the lumen 516 defines an interior portion of a femoral artery 514, but the lumen could define another tissue interior wall.

The distal end 507 of the carrier tube 504 also includes an anchor 506 and a sealing plug 510. The anchor 506 is an elongated, stiff, low-profile member preferably made of a biologically resorbable polymer. The sealing plug 510 is formed of a compressible sponge or foam, made of a hemostatic biologically resorbable material such as collagen, and may be configured in any shape so as to seal the tissue puncture 501.

The sealing plug 510 and anchor 506 are connected to one another by a suture, thread, or filament 502 that is also biologically resorbable. The suture 502 extends distally from the first end 503 of the closure tool 500 through the carrier tube 504. The suture 502 can be threaded through the sealing plug, then through a hole in the anchor 506 and proximally back through the carrier tube 504 to the sealing plug 510. The suture 502 is preferably threaded through a perforation or series of perforations in the sealing plug 510. The suture 502 can also be threaded around itself to form a slip-knot. The suture 502 thus can connect the anchor 506 and the sealing plug 510 in a pulley-like arrangement that serves to cinch the anchor 506 and the sealing plug 510 together when the carrier tube 504 is pulled away from the anchor 506 and the sealing plug 510, sandwiching and locking the anchor and plug together and thereby sealing the tissue puncture 501.

The carrier tube 504 also includes a compaction device, such as a tamping tube or compaction tube 505, for tamping the sealing plug 510 along the suture 502 and against the anchor 506. The compaction tube 505 is shown located within the carrier tube 504 and proximal of the sealing plug 510. The compaction tube 505 is an elongated tubular member that can be rigid or flexible and formed of any suitable material. The suture 502 extends through the compaction tube 505 but is not directly connected thereto. Accordingly, the suture 502 and compaction tube 505 are free to slide past one another. Referring to the embodiment of FIG. 5, the suture 502 extends beyond a proximal end of the compaction tube 505 and attaches to an automatic driving mechanism 730 located within a housing 520 at the first end 503 of the closure tool 500.

In practice, the carrier tube 504 of the closure tool 500 (containing the suture and sealing plug) can be inserted into an insertion sheath 524, which is already inserted within the artery 514. As the closure tool 500 and the associated closure elements are inserted into the insertion sheath 524, the anchor 506 passes through and out of a distal end 509 of the insertion sheath 524 and is inserted into the artery or other tissue lumen 516. The tissue puncture closure tool 500 can then be withdrawn from the insertion sheath 524 until the anchor 506 catches on the distal end 509 of the insertion sheath 524 and rotates to the position shown in FIG. 5. When resistance to further retraction of the closure tool 500 is felt by an operator, the closure tool 500 and the insertion sheath 524 can be withdrawn together, causing the anchor 506 to anchor itself within the artery 514 against the artery wall 511. With the anchor 506 anchored within the artery 514 at the puncture site 501, further retraction of the closure tool 500 and insertion sheath 524 causes the sealing plug 510 to withdraw from the distal end 507 of the carrier tube 504, thereby depositing the plug within the incision or puncture tract 501.

However, unlike the initial closure tool described above, and similar such closure tools that require a separate, manual tamping procedure following the deposition of the sealing plug 510, the tissue puncture closure tool 500 automatically tamps the sealing plug 510. The automatic driving mechanism 730 drives, via a rack or compaction tube driver 744, the compaction tube 505 toward the sealing plug 510 automatically upon withdrawal of the closure tool 500 from the puncture tract, tamping the plug toward the anchor 506 as shown in FIG. 6. The rack or compaction tube driver 744 can be coilable or can be a linear rack. The sealing plug 510 is tamped while the carrier tube 504 is still arranged adjacent to the puncture 501 in the femoral artery 514, reducing or eliminating any gaps that may otherwise occur between the sealing plug 510 and the puncture 501 in the femoral artery 514.

In addition, by placing tension on or pulling the suture 502 away from the puncture tract 501, the suture 502 cinches and locks (with a slip knot or the like) together the anchor 506 and the sealing plug 510, sandwiching the artery wall 511 between the anchor 506 and sealing plug 510. The force exerted by the compaction tube 505 and the cinching together of the anchor 506 and sealing plug 510 by the filament 502 also causes the sealing plug 510 to deform radially outward within the puncture tract and function as an anchor on the proximal side of the tissue puncture site 501.

It is understood that the sealing of a puncture in an artery or other blood vessel wall is given as an example, and that the closure device can be used for sealing other tissue punctures, with the anchor sealing the interior surface of the tissue lumen and the sealing plug providing additional hemostasis in the puncture tract. Applications of closure tools, including those implementing principles described herein, include closure of a percutaneous puncture or incision in tissue separating two internal portions of a living body, such as punctures or incisions in blood vessels, ducts or lumens, gall bladders, livers, hearts, etc.

An additional level of control over the force applied to the sealing plug may be desired, as the force applied may vary. The tamping forces can be affected by any number of variables, such as the height, as well as location of the sealing plug/collagen plug, design tolerances and assembly of the device, as well as physician abilities. Excessive compaction force between the sealing plug and the anchor could lead to excessive force on the anchor, which could potentially result in anchor bending, which in turn could result in a poor seal of the interior wall of the tissue lumen, and thus, a poor seal of the tissue puncture. If excessive compaction force is exerted on the sealing plug, the excessive force could also potentially damage the artery or other tissue, and/or the sealing plug could enter the tissue/organ lumen or lumen of the artery. Additionally, the original puncture site could become distorted due to excessive compaction force, thereby resulting in an incomplete seal of the puncture site, leading to incomplete hemostasis. The sealing plug, e.g., collagen plug, could be damaged and/or torn due to excessive compaction force, resulting in an incomplete seal. Therefore, there is a need for a tissue puncture closure tool that provides for improved control of the compaction force exerted on the sealing plug, and thus on the tissue puncture, artery, and anchor.

It is noted that, in the drawings, the channel for passage of a filament or suture through a compaction device is consistently labeled "S". The various compaction devices described below can, generally, be used with the tissue closure devices described above. The compaction devices described below that incorporate a rack, including a coilable rack, will most likely be utilized with a closure device having an automatic tamping system.

Figure 7:
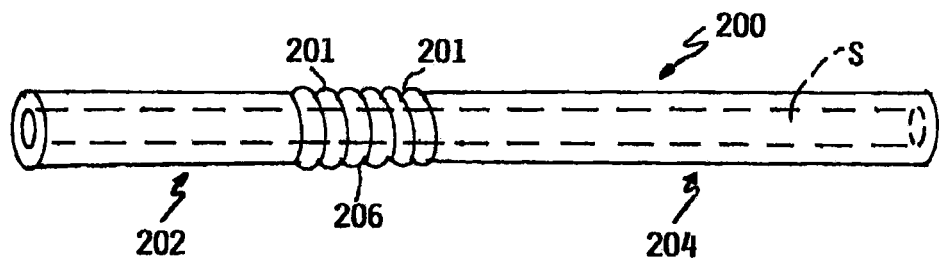
FIG. 7 is a perspective side view of a compaction device tubular member according to one embodiment.
Figure 8:
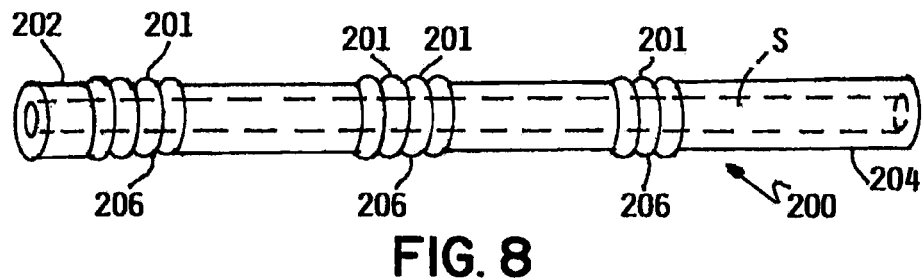
FIG. 8 is a perspective side view of a compaction device tubular member according to one embodiment.

Referring now to FIG. 7, a compaction device, such as a compaction tube 200 or tamping tube, according to one embodiment of the disclosure, is shown. The term tamping tube and compaction tube are used interchangeably, and refer to the tubular member utilized to tamp (compress) the sealing plug; to drive the sealing plug towards the outer surface of a tissue puncture. The compaction tube 200 of FIG. 7, as well as the compaction tubes described in FIGS. 8-29 and 31-45 can be used with the puncture closure tools described above, and other such similar devices. The compaction tube 200 is an elongated tubular member and includes a first or proximal segment 202 and a second or distal segment 204. The proximal segment 202 and the distal segment 204 of the compaction tube 200 can be made of rigid material. The compaction tube 200 further can include an interposed segment 206 coaxially positioned intermediate the proximal segment 202 and the distal segment 204. Intermediate segment 206 can be made of the same or similar material as compared to the material of the proximal segment 202 and the distal segment 204. However, the intermediate segment 206 includes folds or pleats 201 such that, should excessive compaction force be applied to the compaction tube 200, the folds or pleats 201 collapse or accordion, and at least partially absorb applied excessive compaction force and do not transfer all of this excessive compaction force to the sealing plug, tissue puncture, or anchor. Further, as shown in FIG. 8, the compaction tube 200 can include a plurality of segments 206 interspersed along the length of the compaction tube 200.

In another embodiment, the intermediate segment 206 or intermediate segments 206 can be made of a more flexible material than the proximal segment 202 material or the distal segment 204 material. For example, an intermediate segment 206 can be made from thermoplastic elastomers, for example, styrenic block copolymers, polyolefin blends, elastomeric alloys, thermoplastic polyurethanes, thermoplastic polyamides, from silicone, and the like.

Figure 9:
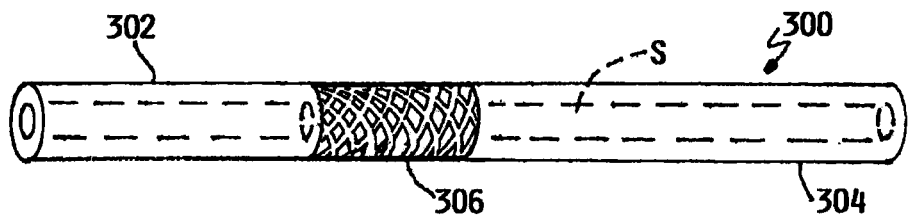
FIG. 9 is a perspective side view of a compaction device tubular member according to one embodiment.
Figure 10:
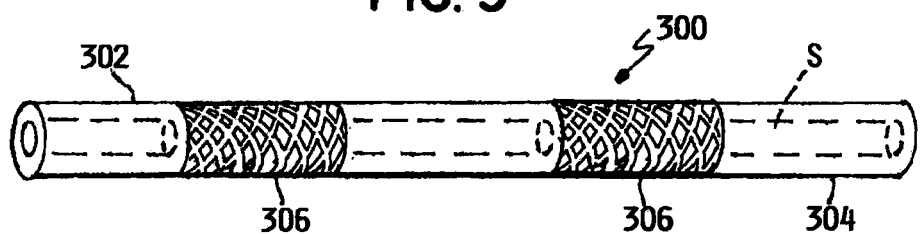
FIG. 10 is a perspective side view of a compaction device tubular member according to one embodiment.

Referring to FIG. 9 there is shown another embodiment of a compaction device 300 of the disclosure. The compaction tube 300 is an elongated tubular member and includes a first or proximal segment 302 and a second or distal segment 304. The proximal segment 302 and the distal segment 304 of the compaction tube 300 can be made of rigid material. The compaction tube 300 further includes an interposed segment 306 coaxially positioned intermediate the proximal segment 302 and the distal segment 304 of the compaction tube 300. The intermediate segment 306 abuts both the proximal segment 302 and the distal segment 304. The intermediate segment 306 includes a web and imparts a lattice-type structure to the intermediate segment 306 of the compaction tube 300. The intermediate segment 306 can be made of a rigid material, such as the proximal segment 302 and the distal segment 304 of the compaction tube 300, or the intermediate segment 306 can be made of a more flexible material. Further, for example, the lattice-type segment 306 can be made of a shape memory material, such as a shape memory polymer or shape memory alloy. Shape memory polymers include materials such as polyurethanes, block copolymers of polyethyleneterephrhalate (PET) and polyethyleneoxide (PEO), block copolymers containing polystyrene and poly(1,4-butadiene), and the like. Shape memory alloys include copper-zinc-aluminum-nickel alloys, copperaluminum-nickel alloys, nickel-titanium alloys (such as nitinol), copper-chromium-nickel alloys (such as Elgiloy®) and the like. Further, as shown in FIG. 10, the compaction tube 300 can include a plurality of lattice-type segments 306 interspersed along the length of the compaction tube 300.

Without being bound by any particular theory, the intermediate segment 306 includes a lattice-type structure such that, should excessive compressive force be applied to the compaction tube 300, the lattice-type structure would buckle, compress, bend, flex, or otherwise absorb at least some of the applied excessive compaction force, such that the sealing plug would be tamped down against the anchor and seal the tissue puncture without damage to the artery, sealing plug, or anchor. Structures other than a lattice-type structure can be present in the compaction tube, for example as generally shown in the other figures, and these other structures can also buckle, compress, bend, flex, or otherwise deform, to absorb at least some of an excessive compaction force applied to a compaction tube.

Figure 11:
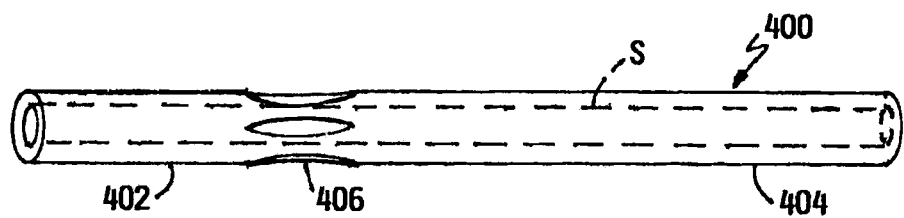
FIG. 11 is a perspective side view of a compaction device tubular member according to one embodiment.
Figure 12:
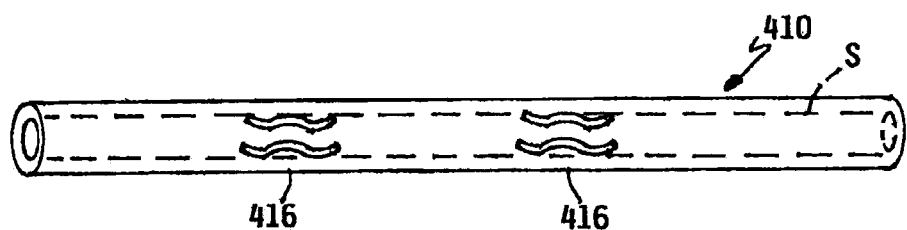
FIG. 12 is a perspective side view of a compaction device tubular according to one embodiment.
Figure 13:
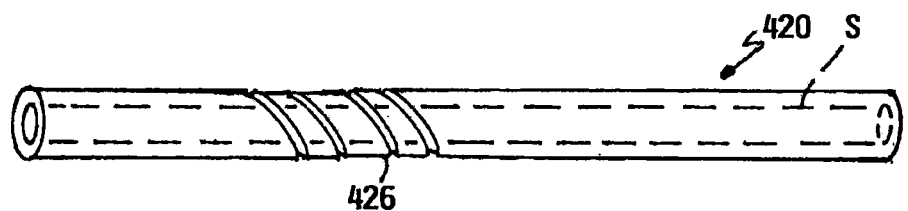
FIG. 13 is a perspective side view of a compaction device tubular member according to one embodiment.

FIG. 11 shows another embodiment of the disclosure, presenting a compaction device 400, wherein the compaction device 400 is an elongated tubular member and includes a first or proximal segment 402 and a second or distal segment 404. The proximal segment 402 and the distal segment 404 of the compaction tube 400 can be made of rigid material. The compaction tube 400 includes at least one segment 406 where sections of material have been removed from the segment 406. The removed sections of material can circumscribe the segment 406 of the compaction tube 400, or the removed sections of material can be arranged in some other pattern around the compaction tube 400. Further, the shape of the section of material removed can vary; for example, the removed shapes can be ovals, ellipses, circles, rectangles, swirls, and the like. The removal of the material allows the compaction tube 400 to compress, flex, bend, compress, buckle, or otherwise absorb at least some applied excessive compaction force. FIG. 11 shows one embodiment of compaction tube 400 with material removed from at least one segment 406 of the tube 400. FIG. 12 shows another embodiment of a compaction tube 410 with swirl cut-outs in segments 416 of the compaction tube 410. Further, FIG. 13 shows a compaction tube 420 with spiral cut-outs in a segment 426 of the compaction tube 420. As will be understood by one skilled in the art, various cut-out shapes and placement of these cut-out shapes are contemplated as embodiments of the disclosure.

Figure 14:
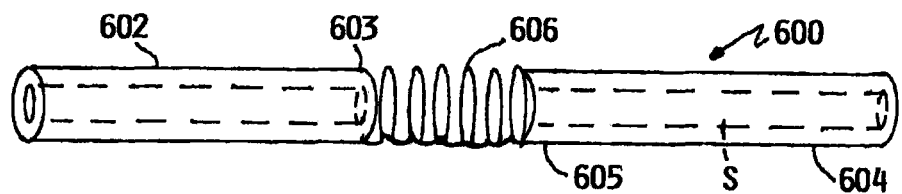
FIG. 14 is a perspective side view of a compaction device tubular member according to one embodiment.
Figure 15:
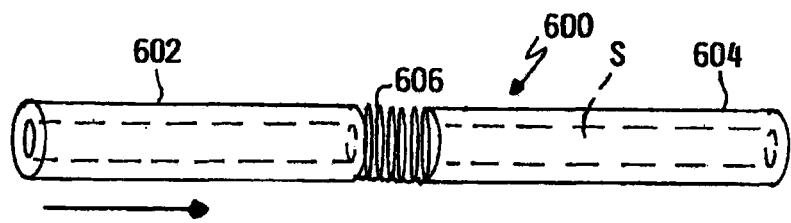
FIG. 15 is a perspective side view of a compaction device tubular member according to one embodiment, where the structure for relieving excessive compaction force is engaged.
Figure 16:
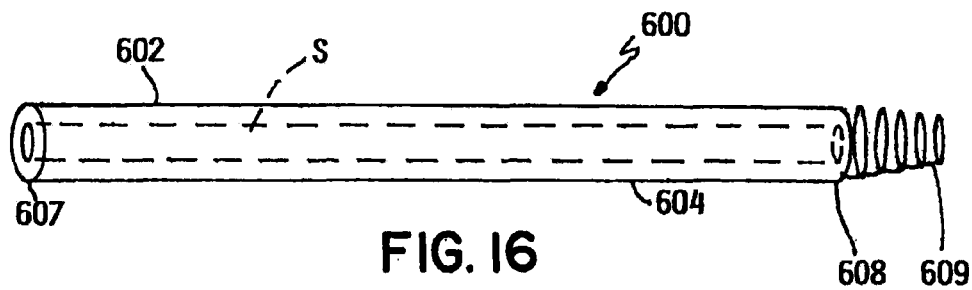
FIG. 16 is a perspective side view of a compaction device tubular member according to one embodiment.
Figure 17:
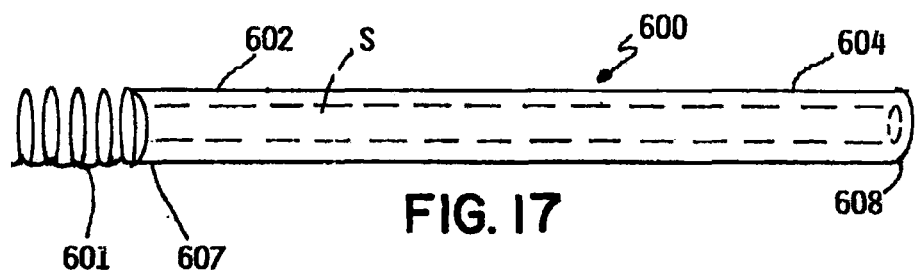
FIG. 17 is a perspective side view of a compaction device tubular member according to one embodiment.

Referring to FIG. 14, yet another embodiment is shown. FIG. 14 shows a compaction device 600, wherein the compaction device 600 is an elongated tubular member having a first or proximal segment 602 and a second or distal segment 604. Coaxially interposed intermediate the proximal segment 602 and the distal segment 604 of the compaction tube 600 is at least one spring 606. FIG. 14 shows an embodiment with a spring 606 bonded between the proximal segment 602 and the distal segment 604 of the compaction tube 600. However, the at least one spring 609, 606, 601 can also be positioned at the distal end 608 or, alternatively, at the proximal end 607 of the compaction tube 600, as shown in FIGS. 16 and 17. The spring 601, 606, 609 can be made from metal, for example, stainless steel, or from a shape memory alloy, and the spring 606 can be bonded to the distal end 603 of the proximal segment 602 of the compaction tube 600 and to the proximal end 605 of the distal segment 604 of the compaction tube 600, such that the spring is sandwiched between the two inner ends 603, 605 of the two tube segments 602, 604; or the spring 609 can be bonded to the distal end 608 of the compaction tube 600 or the spring 601 can be bonded to the proximal end 607 of the compaction tube 600. The spring 606, 601, 609 is designed to compress, bend, flex, buckle, or otherwise deform, when excessive compaction force is applied to the compaction tube 600, the compression, bending, flexing, or other modification of the spring 606, 609, 601 absorbing at least some of the excessive compaction force that would have been applied to the sealing plug, and thus, the anchor and artery or tissue puncture. The compaction tube 600 as shown in FIG. 15 demonstrates the spring 606 of FIG. 14 in a compressed orientation, having at least partially absorbed excessive compaction force from the proximal direction, the direction of the arrow.

Figure 18B:
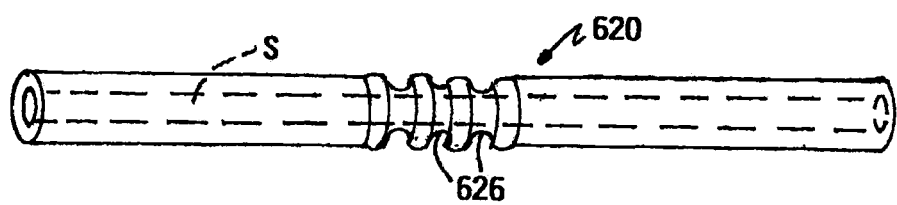
FIG. 18B is a perspective side view of a compaction device tubular member according to one embodiment.

FIG. 18A shows another embodiment, wherein a spring or coil 616, or a plurality of springs or coils 616, circumscribe the through-channel S of the compaction tube 610. Each spring or coil 616 can be embedded in the wall of the compaction tube 610, such that the two ends of the spring or coil 616 meet and circumscribe the through-channel S of the compaction tube 610. The springs and/or coils can be arranged along a segment 618 of the length of the compaction tube 610. Alternatively, the springs or coils 616 can be arranged along the entire length of the compaction tube 610 or in a plurality of segments 618 of the compaction tube 610. In yet another embodiment, as shown in FIG. 18B, the structure 626 represents a thinned tube wall, such that under excessive compaction force the thinned tube walls cause the compaction tube 620 to bend, collapse or deform in some manner.

Figure 18C:
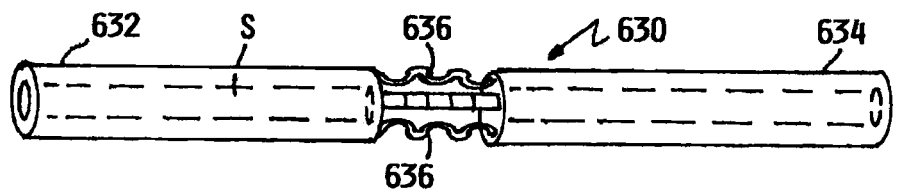
FIG. 18C is a perspective side view of a compaction device tubular member according to one embodiment.

FIG. 18C shows a winding, undulating ribbon, or other spring-like element 636 in a segment of a compaction tube 630, wherein the winding 636, in this example, a sinuous ribbon, is designed to buckle, flex, compress, bend or otherwise deform when subjected to excessive compaction force. The windings, ribbon, or other spring-like elements 636 can be arranged in parallel between two segments 632, 634 of the compaction tube 630, and can be made of elastic polymers, spring steel, stainless steel, or a shape memory alloy.

Figure 19:
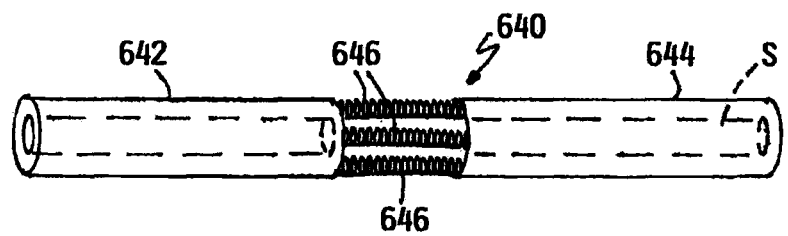
FIG. 19 is a perspective side view of a compaction device tubular member according to one embodiment.
Figure 20:
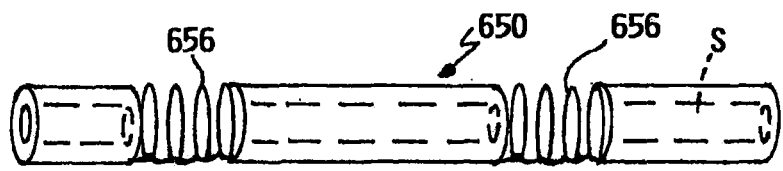
FIG. 20 is a perspective side view of a compaction device tubular member according to one embodiment.
Figure 25:
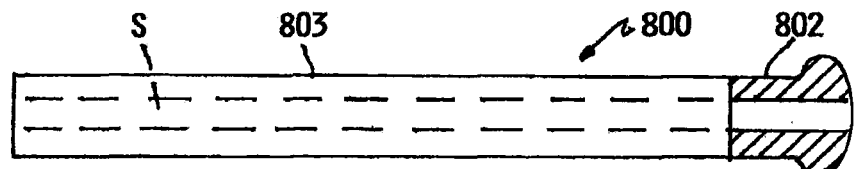
FIG. 25 is a side view of a compaction device tubular member according to one embodiment.
Figure 26:
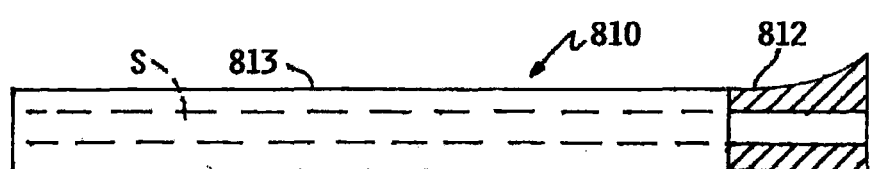
FIG. 26 is a side view of a compaction device tubular member according to one embodiment.
Figure 27:
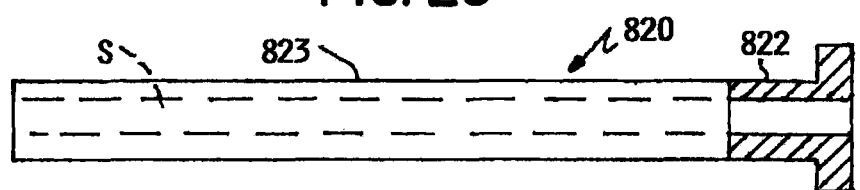
FIG. 27 is a side view of a compaction device tubular member according to one embodiment.

FIG. 19 shows another embodiment of the disclosure, wherein a plurality of springs 646 are arranged in parallel between two segments 642, 644 of the compaction tube 640, wherein the compaction tube 640 has a first or proximal segment 642 and a second or distal segment 644. FIG. 20 shows yet another embodiment of the disclosure, wherein a plurality of springs 656 is coaxially interposed along the length of the compaction tube 650. The springs 646, 656, buckle, compress, flex, bend or otherwise deform when subjected to excessive compaction force, thus absorbing at least some of the excessive compaction force that would have been applied to the sealing plug, and thus to the anchor and/or artery or tissue puncture.

The spring, coil and the winding can take on a number of shapes, including but not limited to a cylindrical shape or a conical shape. It is contemplated, as additional embodiments of the disclosure, that more than one spring, coil or other winding can be interposed along the length of the compaction tube and/or at each end of the compaction tube, and a mixture of springs, coils, and windings can be similarly positioned. Further, the spring, coil, or winding can be made of elastic polymer, stainless steel, spring steel and the like. In another embodiment, the coil, winding, spring-shape is made of a shape memory alloy. Thus, the coil, winding, or spring-like structure can deform when an excessive compaction force is applied to the compaction tube, but can also return to its respective original shape when the excessive compaction force is relieved. Examples of such shape memory alloys include copper-zinc-aluminum-nickel alloys, copper-aluminum-nickel alloys, nickel-titanium alloys (such as nitinol), copper-chromium-nickel alloys (such as Elgiloy®), and the like.

Another embodiment of the disclosure is shown in FIGS. 21-22. FIG. 21 shows a compaction device 700 that is composed of two separate tubular members 701, 702. Compaction device 700 is an elongate construction having a first or proximal end 703 and a distal or second end 706. Two separate tubular members 701, 702, compose the compaction device 700. A first tubular member 701 has a first or proximal end 703 and a distal or second end 705, and a second tubular member 702 has a proximal or first end 704 and a distal or second end 706. The first tubular member 701 has an outer diameter $OD_1$ and the second tubular member 702 has an inner diameter $ID_2$, where the outer diameter $OD_1$ is smaller than the inner diameter $ID_2$, such that the first tubular member 701 can fit within the second tubular member 702. As noted above, first and second tubular members 701 and 702 compose the compaction device 700; the distal end 705 of the first tubular member 701 is fitted within the proximal end 704 of the second tubular member 702. The fit between the distal end 705 of the first tubular member and the proximal end 704 of the second tubular member is structurally stable, such that the distal end 705 is substantially immovably secured in position within the proximal end 704, and the thus formed compaction device 700 has the column strength to perform the function of an integrally formed compaction tube. The exterior surface 707 of the first tubular member 701 works together with the interior surface 708 of the second tubular member 702 to restrict motion of the first tubular member 701 within the second tubular member 702. This restriction of motion can be accomplished in any number of ways, for example, the exterior surface 707 of the first tubular member 701 and/or the interior surface 708 of the second tubular member 702 can include a coating 709 that restricts movement of the tubular members 701, 702 relative to one another; the material of the first tubular member 701 and the material of the second tubular member 702 can have a high coefficient of friction that restricts movement of the tubes 701,702 relative to each other; the exterior surface 707 of the first tubular member 701 and/or the interior surface 708 of the second tubular member 702 can include protuberances such as nubs, knobs, bumps, fingers, and the like 710, which restrict the movement of the first tubular member 701 within the second tubular member 702.

The examples of methods of restricting the movement of the tubular members 701, 702 relative to one another are exemplary in nature, and not limiting. Other methods can be used to restrict this relative movement. However, whichever method is used to restrict the relative movement of the tubular members 701, 702, the force maintaining the tubular members 701, 702 substantially immovably secured in position is overcome when excessive compaction force is applied to the compaction device 700, such that the first tubular member 701 slidingly engages with the second tubular member 702, to at least partially absorb excess compaction force. In operation, compaction device 700, comprising two tubular members 701, 702, is used to tamp a sealing plug into place within an incision or tissue puncture. During the tamping process, the first tubular member 701 and the second tubular member 702 are structurally stable relative to one another, having the column strength to form compaction device/tube 700. If/when excessive compaction force is applied to the compaction tube 700, column strength is lost, and first tubular member 701 disengages from a substantially immovably secure position within second tubular member 702, slidingly engages the second tubular member 702, with the first tubular member 701 distal end 705 moving towards the second tubular member 702 distal end 706, thus absorbing at least part of applied excessive compaction force and preventing damaging and/or mis-positioning the sealing plug and/or the anchor.

FIG. 23 shows an alternate configuration of the compaction device 700 of FIGS. 21 and 22. In FIG. 23 a plurality of tubular members, in this case three tubular members 752, 754, 756, compose the compaction device 750. The first tubular member 752 has a proximal end 760 and a distal end 751, the second tubular member 756 has a proximal end 755 and a distal end 757, and the third tubular member 754 has a proximal end 753 and a distal end 762. The first and third tubular members 752, 754 have an inner diameter $ID_2$ and the second tubular member 756 has an outer diameter $OD_1$, where the outer diameter $OD_1$ is smaller than the inner diameter $ID_2$, such that the second tubular member 756 can fit within the first and third tubular members 752, 754. The proximal end 755 of the second tubular member 756 is fitted within the distal end 751 of the first tubular member 752, and the distal end 757 of the second tubular member 756 is fitted within the proximal end 753 of the third tubular member 754. As above, the fit among the three tubular members 752, 756, 754, is structurally stable, such that the distal and proximal ends 757, 755 of the second tubular member 756 are substantially immovably secured in position within the distal end 751 and proximal end 753 of the first and third tubular members 752, 754, respectively, and the thus formed compaction device 750 has the column strength to perform the function of an integrally formed compaction tube. The exterior surface 763 of the second tubular member 756 works together with the interior surface 765, 767, of the first and third tubular members 752, 754 to restrict motion of the third tubular member 756. This restriction of motion can be accomplished similarly to the two tubular member compaction tube described above, and also similarly, the tubular members will move relative to one another when sufficient excessive compaction force is applied, to at least partially absorb excessive compaction force; the second tubular member 756 slidingly engaging both the first and third tubular members 752, 754.

In yet another embodiment, as shown in FIG. 24, first and second tubular members 782, 784 compose compaction device 780. The first tubular member 782 has an outer diameter $OD_1$ that is smaller than the inner diameter $ID_2$ of the second tubular member 784. Further, the second tubular member 784 includes a chamber 786 at its proximal end 785, such that the distal end 783 of the first tubular member 782 can be fitted within the chamber 786. In one embodiment, the chamber is a cylindrical chamber 786, the interior surface 788 of the second tubular member 784 forming the walls of the chamber 786, and an annular surface forming the base 790 of the chamber 786. The base 790 is positioned perpendicular to the longitudinal axis of the second tubular member 784. A spring 789 can be coupled to the base 790, such that the spring 789 is adapted to engage the distal end 783 of the first tubular member 782. When/if excessive compaction force is exerted on the compaction device 780, the first tubular member 782 slidingly engages the second tubular member 784, traveling distally in the chamber 786, and encounters and engages the spring 789. The spring 789 at least partially absorbs excessive compaction force, and when the excessive compaction force is removed, the compaction tube 780 returns to its original configuration. The spring 789 is made (e.g., due to material, thickness, and the like) such that the spring 789 does not compress until excessive compaction force is applied to the compaction tube 780.

Figure 28:
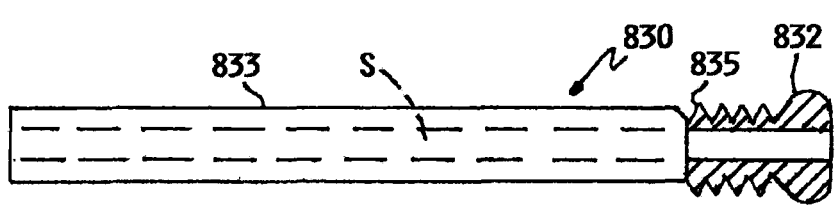
FIG. 28 is a side view of a compaction device tubular member according to one embodiment.
Figure 29:
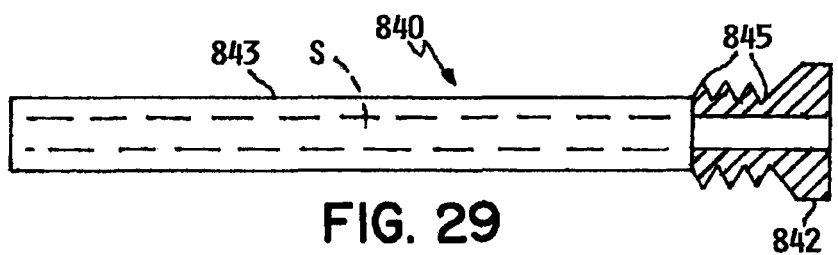
FIG. 29 is a side view of a compaction device tubular member according to one embodiment.

Referring to FIGS. 25-29 there are shown additional embodiments of the present disclosure. FIGS. 25-29 show compaction tubes 800, 810, 820, 830, 840, with variations to the distal section 802, 812, 822, 832, 842, of the compaction tube. Generally, the compaction tubes 800, 810, 820, 830, 840, can have a rigid first or proximal section 803, 813, 823, 833, 843, and a softer, more elastomeric distal section 802, 812, 822, 832, 842. The proximal section 803, 813, 823, 833, 843, of the compaction tube 800, 810, 820, 830, 840, can be made of a rigid material, for example, PEEK (polyetheretherketone), ISOPLAST® (thermoplastic polyurethane resin), GRILAMID® TR55 (transparent polyamide), TROGAMID® (transparent polyamide), polyethylene, and the like, or can be made of metal, such as stainless steel, and the like. The distal section 802, 812, 822, 832, 842, of the compaction tube 800, 810, 820, 830, 840, can be made of a more flexible material than the proximal section 803, 813, 823, 833, 843 material. For example, the distal section 802, 812, 822, 832, 842, can be made from thermoplastic elastomers, for example, styrenic block copolymers, polyolefin blends, elastomeric alloys, thermoplastic polyurethanes, thermoplastic polyamides, from silicone, and the like. Alternatively, the distal section 802, 812, 822, 832, 842, can also be made of a more rigid material similar to the respective proximal section, of stainless steel, for example, and a more flexible material (listed above) can be overmolded onto the rigid material. Further, the distal section 802, 812, 822, 832, 842 can take on a number of alternative shapes, however, in each case the distal section 802, 812, 822, 832, 842, includes a soft/flexible deformable (e.g., compressible, bendable) tip. The combination of the soft/flexible deformable tip and the shape of the tip absorbs at least some of an applied excessive compaction force, to prevent excessive application of force on the sealing plug, and thus, the artery, tissue puncture, and/or anchor. The soft/flexible deformable tip compresses, bends, flexes, spreads, or otherwise deforms upon application of excessive compaction force. Further, the shape of the tip assists in absorbing excessive compaction force and also the shape of the flexible tip results in a larger compaction footprint which assists in ensuring better overall compaction of the sealing plug. The shape of the flexible tip can include a rounded end, anvil end, bullet-nosed, flared end, hollow-pointed, square, and other shapes which provide an expanded surface area as compared to an unaltered tube end. FIGS. 28-29 show a further variation to the above described general structure for the compaction tube, wherein the distal end of the proximal section 833, 843, includes a serrated or accordion shape 835, 845, wherein the serrated or accordion section 835, 845, assists in at least partially absorbing excessive compaction force. The serrated or accordion sections 835, 845, can be mixed and match with various distal end shapes.

Figure 30:
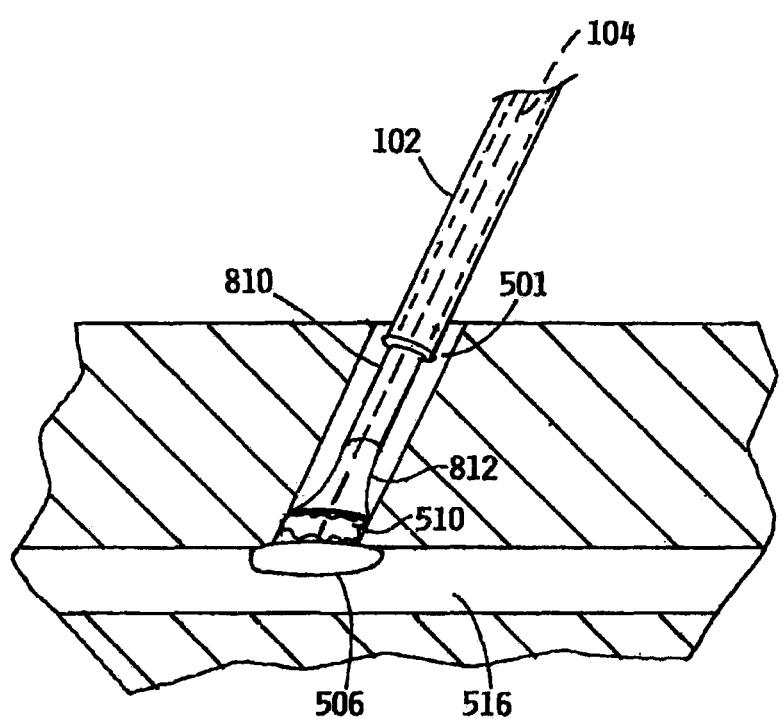
FIG. 30 is a side view of a compaction tube according to one embodiment, inserted in an incision or puncture tract, and tamping the sealing plug.

FIG. 30 shows an example of a compaction tube 810 with a flared or anvil-shaped distal section 812 inserted in an incision or puncture tract 501, with the distal section 812 compressing and setting the sealing plug (collagen plug) 510 against the outer surface of the tissue puncture. The footprint provided by the anvil-shaped distal section 812 assists in providing improved overall compaction of the sealing plug 510.

The various compaction tubes and devices described above can be used with a manual tamping system, as well as with an automatic tamping system, such as the systems described in, for example, U.S. Pat. No. 6,045,569; U.S. Pat. No. 6,090,130; U.S. Pat. No. 7,250,057; U.S. Pat. No. 7,931,670, all herein incorporated by reference. In an automatic tamping system a compaction device can include a rack or compaction driver rack, which can interface with a compaction tube, urging the compaction tube toward the sealing plug. The rack can be a rigid rack or a flexible, coilable rack. The rigid or coilable rack can be used with one of the compaction tubes described above. In addition, the interface between the compaction tube and the rack can assist in at least partially absorbing excessive compaction force. The racks described below can take on various shapes, for example, a tubular shape or a horseshoe-shape or "U" shape, such that the surface presented to the filament or suture 104 is concave. Therefore, the suture 104 and the rack are free to slide past one another.

Figure 31:
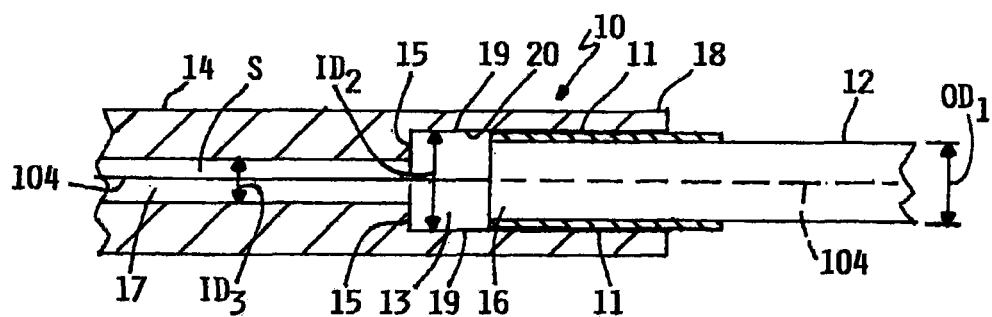
FIG. 31 is a side partial cut-away view according to one embodiment of an interface of a rack and a compaction tube of a compaction device.

FIG. 31 shows one embodiment of a compaction device including a rack 12 and compaction tube 14 interface 10. The outer diameter $OD_1$ of the rack 12 is smaller than the inner diameter $ID_2$ of a chamber 13 disposed in the proximal end 18 of the compaction tube 14. An annular surface forms the base 15 of the chamber 13 such that the channel 17 extending distally from the base 15 has a diameter $ID_3$, smaller than the outer diameter $OD_1$ of the rack 12. The channel 17 is adapted to accommodate the suture that passes to the sealing plug and anchor. The distal end 16 of the rack 12 is fitted to be received by the chamber 13 in the proximal end 18 of the compaction tube 14. In operation, as the rack 12 travels distally towards the compaction tube, sealing plug, and anchor, the distal end 16 of the rack 12 engages with the chamber 13 in the proximal end 18 of the compaction tube 14. A friction fit interface 11 between the distal end 16 of the rack 12 and the walls 19 of the chamber 13 maintains the distal end 16 substantially immovable within the chamber 13. However, when excessive compaction force is applied to the compaction tube 14, the friction fit interface 11 collapses, and the distal end 16 of the rack 12 is released and allowed to travel further along the chamber 13, thereby at least partially absorbing excessive compaction force. The friction fit interface 11 can be created in various ways, for example, by creating a tight fit between the distal end 16 of the rack 12 and the chamber walls 19; by coating the exterior surface of the distal end 16 of the rack 12 and/or the interior surface 20 of the chamber 13; by including additional structure, for example, bumps, fingers, nubs, or other protrusions on the interior surface 20 of the chamber 13 and/or on the exterior surface of the distal end 16. In another embodiment, a spring can be coupled to the base 15 of the chamber 13, to assist in absorbing excessive compaction force applied to the compaction device.

It should be noted that the proximal end 18 of the compaction tube can just be a tubular section of the compaction tube 14, wherein the diameter $ID_2$ of the compaction tube 14 is the same throughout the compaction tube 14. When excessive compaction force is applied to the compaction tube 14, the friction fit interface 11 collapses, and the distal end 16 of the rack 12 is released and allowed to travel along the length of the compaction tube 14, thereby at least partially absorbing excessive compaction force. The compaction tube 14 can also include a flexible tip, as described above, at its distal end.

Figure 32:
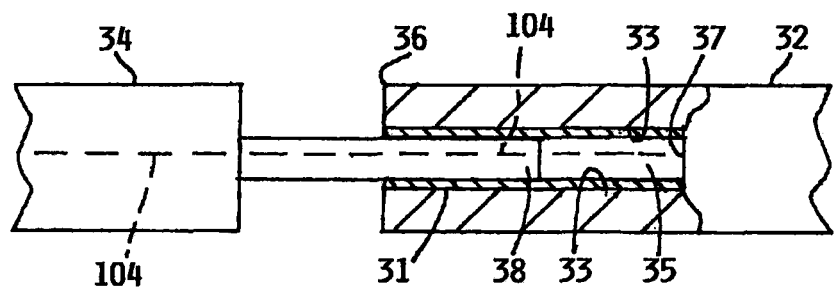
FIG. 32 is a side partial cut-away view according to one embodiment of an interface of a rack and a compaction tube of a compaction device.
Figure 33:
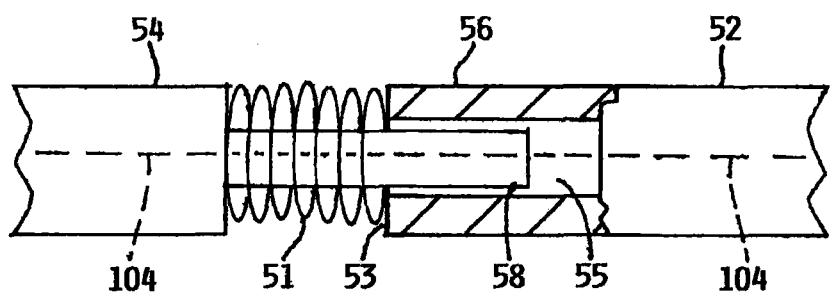
FIG. 33 is a side partial cut-away view according to one embodiment of an interface of a rack and a compaction tube of a compaction device.

Alternatively, FIG. 32 shows an embodiment wherein a proximal segment 38 of the compaction tube 34 is fitted to engage with a chamber 35 formed in the distal end 36 of the rack 32. Here, too, in operation, as the rack 32 travels distally towards the compaction tube 34, sealing plug, and anchor, the walls 33 of the chamber 35 in the distal end 36 of the rack 32 engage with the proximal end 38 of the compaction tube 34. A friction fit interface 31 between the proximal end 38 and the chamber walls 33 maintains the proximal end 38 substantially immovable within the chamber 35. However, when excessive compaction force is applied to the compaction tube 34, the friction fit interface 31 collapses, and the proximal end 38 of the compaction tube 34 is released and allowed to travel further along the chamber 35, to the base 37, thereby at least partially absorbing excessive compaction force. The friction fit interface 31 can be created in various ways as noted in the above examples associated with FIGS. 21, 22, 31. FIG. 33 shows yet another embodiment, wherein a proximal segment 58 of the compaction tube 54 is fitted to enter a chamber 55 formed in the distal end 56 of the rack 52. In operation, as the rack 52 travels distally towards the compaction tube 54, sealing plug, and anchor, the proximal end 58 of the compaction tube 54 enters the chamber 55 in the distal end 56 of the rack 52. Under excessive compaction force, the distal end surface 53 of the rack 52 will engage with spring 51, thus at least partially absorbing excessive compaction force. As noted in the above examples, the structure for the compaction tube in one example can become the structure for the rack in another example, and the complementary structure for the rack can become the structure for the compaction tube.

Figure 34:
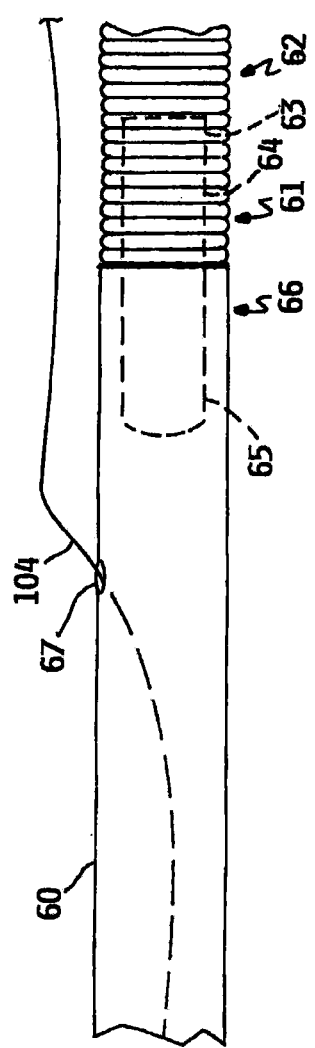
FIG. 34 is a side view of a compaction device comprising a compaction tube, coilable rack and connector therebetween, according to one embodiment.

In another aspect, as shown in FIG. 34, there is shown a coilable rack, for example, a coiled wire. The coilable rack 62 can be made of elastic polymer, metal, metal alloys, or composites, for example, from stainless steel or nitinol. Further, the coilable rack 62 can be coated. The coilable rack 62, in this example, is a coiled wire. The coilable rack 62, as previously noted, can travel in a circular path in a cam type deployment, circular track and gear type deployment, for example. Alternatively, the coilable rack 62 can travel in a linear path. The proximal end of the coilable rack 62 can be driven by, for example, a pin, a cam, a spring, or the like. The distal end portion 61 of the coilable rack 62 interfaces with a compaction tube 60, to tamp the sealing plug into place. The interface mechanism between the compaction tube 60 and the coilable rack 62 can be a connector, for example, a spacer, a core wire, and the like, as well as press-fits, tipping, thermal bonding, adhesive bonding, and the like. Generally, the exterior profile of the transition between the compaction tube 60 and the coilable rack 62 is designed to be relatively smooth, complementing the exterior profile of the compaction tube 60 and the coilable rack 62, facilitating smooth operation of the closure device. Referring to FIG. 34 there is shown a spacer 64 disposed between the coilable rack 62 and the compaction tube 60. The proximal end portion 63 of the spacer 64 is disposed in the lumen of the distal end portion 61 of the coilable rack 62. The distal end portion 65 of the spacer is disposed in the proximal end portion 66 of the compaction tube 60. The proximal end portion 63 of the spacer 64 can be coupled to the distal end portion 61 of the coilable rack; for example, the proximal end portion 63 of the spacer 64 can be plasma welded to the distal end portion 61 of the coilable rack 62. Whatever method is used to couple the spacer 64 to the coiled rack 62, for example, welded or thermal or adhesive bonded, the detachment force between the spacer 64 and coiled rack 62 is greater than the detachment force between the spacer 64 and compaction tube 60. Thus, the compaction tube 60 can be disengaged from the spacer 64 and the coiled rack 62 and, for example, the compaction tube 60 could still be used to manually tamp the sealing plug. The combination of the compaction tube 60, spacer 64 and coilable rack 62 may be too unwieldy or uncomfortable for use as a manual tamping device. Further, the compaction tube 60 in the embodiment shown in FIG. 34 includes an aperture 67 through which a filament or suture 104 can pass, as the suture 104 travels distally from the proximal end of the closure device, through the aperture 67 in the compaction tube 60, and further distally through the compaction tube 60, to the sealing plug and anchor.

Figure 41:
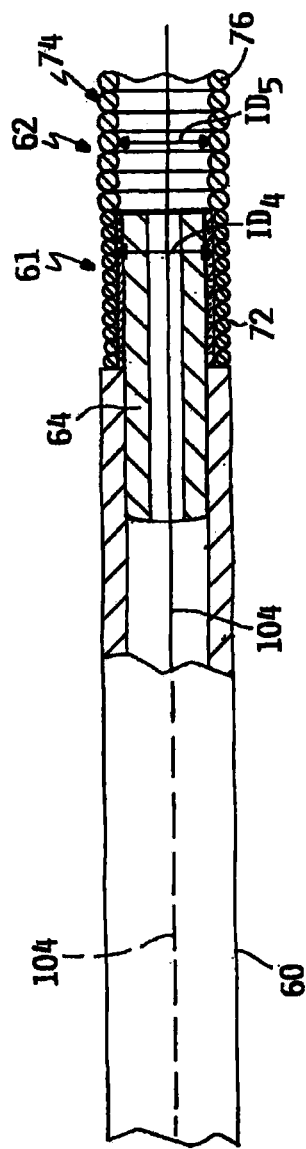
FIG. 41 is a side partial cut-away view of a compaction tube, coilable rack and connector/spacer, wherein the coils of the coilable rack are of different sizes, according to one embodiment.

As noted above, the coilable rack 62 can be coupled to the spacer or connector 64 using a variety of methods. Plasma welding the distal end portion 61 of the coilable rack 62 to the proximal end portion 63 of the spacer, forming a bond 75, is but one example. Generally, in the examples above and below, the compaction tube 60 can be engaged with the coilable rack 62, with or without a connector therebetween. The compaction tube 60 and coilable rack 62 combination structure can be fixed when the closure device is produced (with or without a connector) or, alternatively, the compaction tube 60 can engage with the coilable rack 62 (with or without a connector) during the performance of the closure device. Referring to FIG. 35, there is shown a cut-away view of a compaction tube 60, spacer 64 and coilable rack 62, wherein the coilable rack 62 is coupled 75 to the spacer 64. The coupled area 68 can be long or short dependent upon a number of factors including, but not limited to, coupling method used, stressors impinging the coupled area 68, and stiffness or flexibility required in the coupled area 68. The spacer 64 shown in FIG. 35 is a relatively or completely solid spacer 64, therefore the compaction tube 60 includes an aperture 67 in a surface of the compaction tube 60, such that a suture 104 can pass into the compaction tube 60. The spacer 64 can also be a core wire or other connector. Alternatively, the spacer 64 can include a through lumen, as shown in FIG. 36, such that a suture 104 can travel from the proximal end of the closure device, through the lumen formed by, for example, the coil of the coilable rack 62, through the lumen of the spacer 64 and distally on through the lumen of the compaction tube 60 to the sealing plug and anchor. FIG. 41 also shows a hollow tube that serves as the spacer 64, such that a suture 104 can travel distally from the proximal end of the closure device to the sealing plug and anchor, through the coilable rack 62, hollow tube spacer 64 and compaction tube 60. FIG. 41, in addition, shows that the wire or other material composing the coils 72 is not required to have the same cross-sectional diameter throughout the coilable rack 62. For example, the distal end portion 61 of the coilable rack 62 can comprise smaller diameter wire cross-sections as compared to the larger diameter wire cross-sections in the remainder of the coilable rack 62, including the proximal end portion 74, such that the diameter of the lumen $ID_4$ of the distal end portion 61 of the coilable rack 62 is larger than the diameter of the lumen $ID_5$ of the proximal portion 74 of the coilable rack 62. Wires of two different diameter cross-sections can be fixed together, for example, to provide for a coilable rack with different coils 72. A larger diameter lumen $ID_4$ of the distal end portion 61 of the coilable rack 62 is adapted to accept a larger spacer, connector or core wire 64, whereas coils 72 of larger diameter wire cross-sections of the proximal end portion 74 of the coilable rack 62 provide for additional column strength. As noted above, the spacer 64 can be a wire, for example, a core wire, in which case FIG. 35 shows the likely configuration of the compaction tube 60, with an aperture 67 in the surface of the compaction tube 60 to accommodate the passage of a suture 104.

Figure 37A:
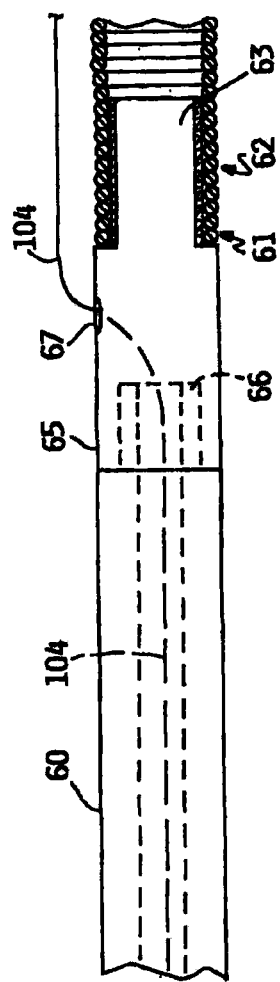
FIG. 37A is a side partial cut-away view of a compaction tube, coilable rack and connector/spacer with an end of the compaction tube disposed in the lumen of the spacer, according to one embodiment.
Figure 42:
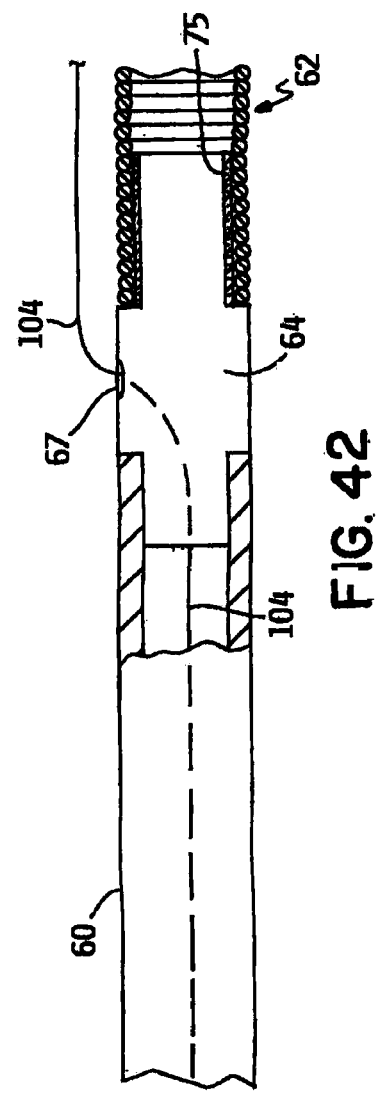
FIG. 42 is a side partial cut-away view of a compaction tube, coilable rack and connector/spacer according to one embodiment.

In another embodiment, the spacer 64 can include an aperture to accommodate passage of a suture 104, as shown in FIG. 42. Alternatively, the spacer 64 can be a recessed spacer 64, whereby a suture 104 passes through the recess of the spacer. FIG. 37 shows one example of a spacer 64 with a recess 69. The shape of the spacer 64 can vary, so long as a proximal end portion 63 of the spacer 64 is in contact with the coilable rack 62 and a distal end portion 65 of the spacer 64 is in contact with the compaction tube 60. The recess 69 in the spacer 64 provides a suture 104 with access to the lumen of the compaction tube 60. The recess 69 in the spacer 64 provides access to a chamber through which a suture 104 can travel distally, through the compaction tube 60, and further distally to the sealing plug and anchor. FIG. 38 shows a cross-section of the spacer 64, through the recess 69, with a suture 104 occupying the recess 69, as the suture 104 passes to the compaction tube 60. FIG. 37A shows a side view of a compaction tube 60, spacer 64, and coilable rack 62, where the distal end portion 65 of the spacer 64 envelops the proximal end portion 66 of the compaction tube 60 such that the proximal end portion 66 of the compaction tube 60 is within the lumen of the distal end portion 65 of the spacer 64. The proximal end portion 63 of the spacer 64 is disposed within the lumen formed by the distal end portion 61 of the coilable rack 62. An aperture 67 in the spacer 64 provides access for a suture 104 to pass distally through the lumen of the compaction tube 60.

Figure 39:
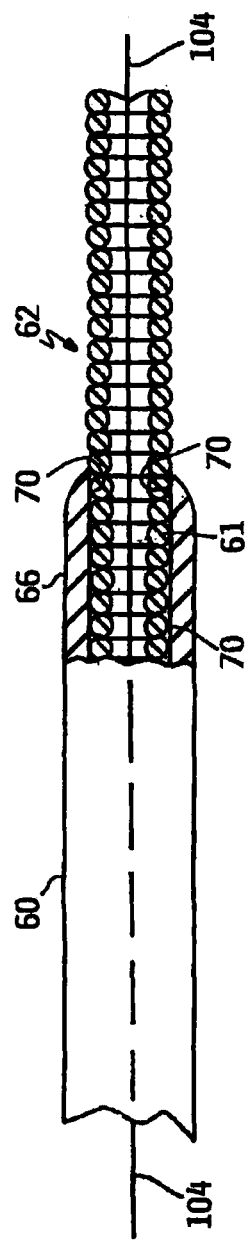
FIG. 39 is a side partial cut-away view of a compaction tube and coilable rack, press-fit according to one embodiment.
Figure 39A:
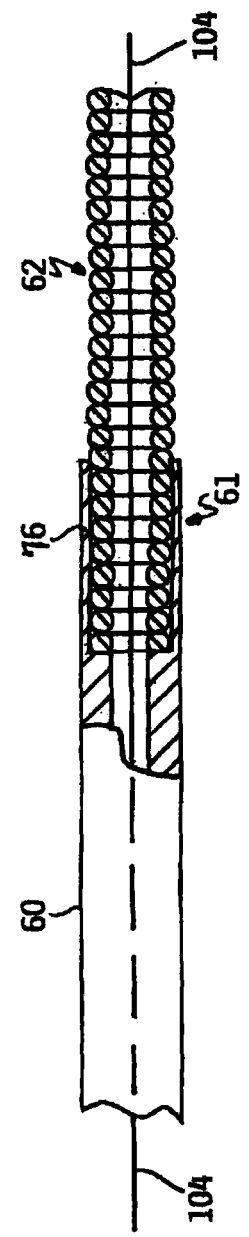
FIG. 39A is a side partial cut-away view of a compaction tube and coilable rack, press-fit according to one embodiment.

The compaction tube 60 and the coilable rack 62 can be engaged with each other without the use of a spacer, core wire, or some other connector 64. The compaction tube 60 and the coilable rack 62, for example, can be press-fit together, and still have the column strength to tamp the sealing plug into place, and yet at least partially absorb excessive compaction force. Referring now to FIGS. 39, 39A, the coilable rack 62 engages with the proximal end portion of the compaction tube 60, wherein the proximal end portion of the compaction tube 60 is tipped. The proximal end portion 66 of the compaction tube 60 can have a different shape as compared to the rest of the compaction tube; for example, the end can be flared, the tube walls 76 can be thinned, the tube end can be tapered, thus forming a neck, and the like. The distal end portion 61 of the coilable rack 62 engages with the interior wall 70 of the tipped proximal end portion 66 of the compaction tube 60. The interior wall 70 of the tipped proximal end portion 66 of the compaction tube 60 at least exerts some force on the proximal end portion 61 of the coilable rack 62, such that the proximal end portion 61 of the coilable rack 62 is maintained in place in the tipped proximal end portion 66 of the compaction tube 60. Thus, the distal end portion 61 of the coilable rack is press-fit into the tipped proximal end portion 66 of the compaction tube 60.

In yet another embodiment, as shown in FIG. 40, the proximal end portion 66 of the compaction tube 60 engages with the distal end portion 61 of the coilable rack 62, such that the proximal end portion 66 of the compaction tube 60 is fitted into the distal end portion 61 of the coilable rack 62. The proximal end portion 66 of the compaction tube 60 is narrowed such that the narrowed portion can fit into the distal end portion 61 of the coilable rack 62. In one embodiment, the compaction tube 60 forms a narrowed neck portion 71 wherein the narrowed neck portion 71 fits within the distal end portion 61 of the coilable rack 62. In another embodiment, the proximal end portion 66 of the compaction tube 60 comprises at least one prong 73 wherein the at least one prong 73 fits within the distal end portion 61 of the coilable rack 62 (see FIG. 40A). Preferably, the proximal end portion 66 of the compaction tube 60 comprises a plurality of prongs 73, and more preferably, the proximal end portion 66 of the compaction tube 60 comprises a narrowed neck portion 71, wherein longitudinal segments of the narrowed neck portion 71 have been removed, forming a plurality of prongs 73, wherein the prongs 73 can have some spring or elasticity, such that the prongs 73 exert a force against the distal end portion 61 of the coilable rack 62, as the distal end portion 61 of the coilable rack 62 exerts a containing force against the prongs 73. In another embodiment, the distal end portion 66 of the compaction tube 60 can include a plurality of prongs 73 about the perimeter of the distal end portion 66 of the compaction tube sized such that the distal end portion 61 of the coilable rack 62 fits within the lumen formed by the prongs 73.

The above described embodiments provide for a compaction tube, or compaction tube coilable rack combination, that can tamp the sealing plug into place. Additionally, the various embodiments can absorb at least some of an excessive tamping force, if/when an excessive tamping force is exerted.

Other tissue puncture closure tools, as described in U.S. Pat. No. 7,749,248, herein incorporated by reference, for example, incorporate an at least partially coiled tamping device for advancing the sealing plug toward the outer surface of the tissue puncture. The tissue puncture closure tool can include a spool at the first end, such that the portion of the tamping device coiled on the spool is flexible, and the portion of the tamping device that is uncoiled and adjacent to the sealing plug is stiff. Generally, the tamping device may extend through a shaper such that a portion of the tamping device proximal of the shaper comprises a flexible configuration and a portion of the tamping device distal of the shaper comprises a straight, stiff configuration. The tamping device passes through a shaper and a cross-sectional shape of the tamping device is altered, for example, to stiffen the tamping device.

Alternatively, the tamping device can comprise a first longitudinal section at least partially coiled on a first spool and a second longitudinal section at least partially coiled on a second spool. The shaper then integrates the first longitudinal section of the tamping device coiled on the first spool and the second longitudinal section of the tamping device coiled on the second spool into a stiff, generally straight member. Accordingly, each of the first and second longitudinal sections can comprise semi-circles in cross-section.

In another embodiment, the tamping device can include a chain that is flexible in a first coiling direction but rigid in a direction opposite of the first coiling direction.

Tamping of the sealing pad to seal the tissue puncture using one of the types of tissue puncture closure devices described above may be improved to provide better consistency and control over the force applied to the sealing pad by using a tamping device of the disclosure.

Figure 43:
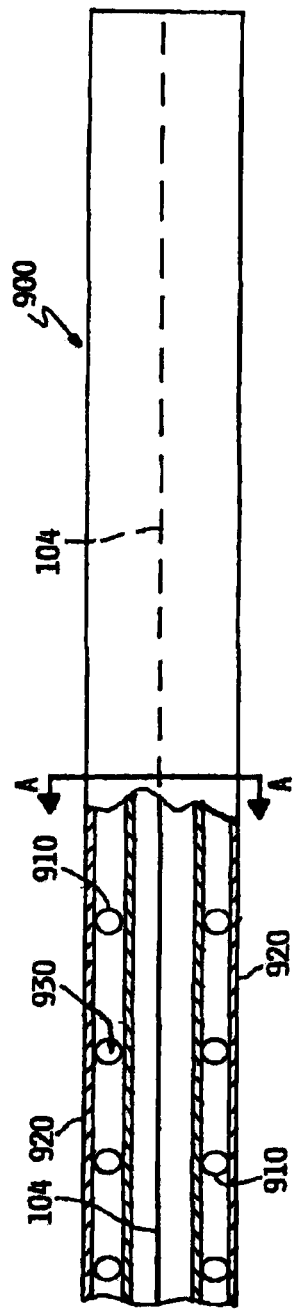
FIG. 43 is a side partial cut-away view of a coilable compaction device according to one embodiment.

Referring to FIG. 43, the coilable tamping device or compaction device 900, provides the column strength required to tamp a sealing plug towards the anchor, and yet the compaction device 900 is deformable under excessive compaction force such that at least some of the applied excessive compaction force is absorbed and not transferred to the tissue puncture, sealing plug, anchor, or artery. The coilable compaction device 900 can include a plurality of coils 910 embedded in or overcoated with a flexible polymer. The flexible polymer, such as Tecothane®, can be reflowed or overflowed on top of the coils 910, where the coils 910 are spaced apart and arranged in the walls of the polymer structure, for example, in the walls of a polymer tube 920. The coils can be arranged in a pattern, for example, in parallel, along the length of the polymer tube 920. The coils 910 can be aligned such that each coil circumscribes the polymer tube 920; that an axis passing through the center of the aperture 930 of the coil 910 circumscribes the polymer tube 920 and is in a plane perpendicular to the plane of the longitudinal axis of the polymer tube 920. In operation, the flexible polymer tube 920, with the assistance of the coils 910, is coilable yet, uncoiled, the compaction tube 900 (comprising the coils 910 and the polymer tube 920) has the column strength to adequately tamp the sealing plug towards the anchor, to seal the tissue puncture. Further, the presence of the coils 910 and the flexible polymer assist the compaction device 900 in absorbing at least some of an applied excessive compaction force, by causing the compaction device 900 to deform, for example, by buckling, compressing, or collapsing, such that excessive compaction force is not applied to the sealing plug, causing damage to the sealing plug, anchor, tissue puncture, or artery. FIG. 45 is another embodiment of a compaction device 950 wherein the coils 960 are similarly aligned as the coils in FIG. 43, however, the coils 960 are arranged in groups, each groups consisting of a plurality of coils 960, as compared to the individually spaced apart coils 910 as shown in FIG. 43. In operation, the coils 960 and the polymer tube 970, composing the compaction device 950 in FIG. 45, perform similarly to the coils 910 and the polymer tube 920 of the compaction device 900 shown in FIG. 43. FIG. 46 shows a cross-section of the compaction device 900 at the line A-A.

Figure 44:
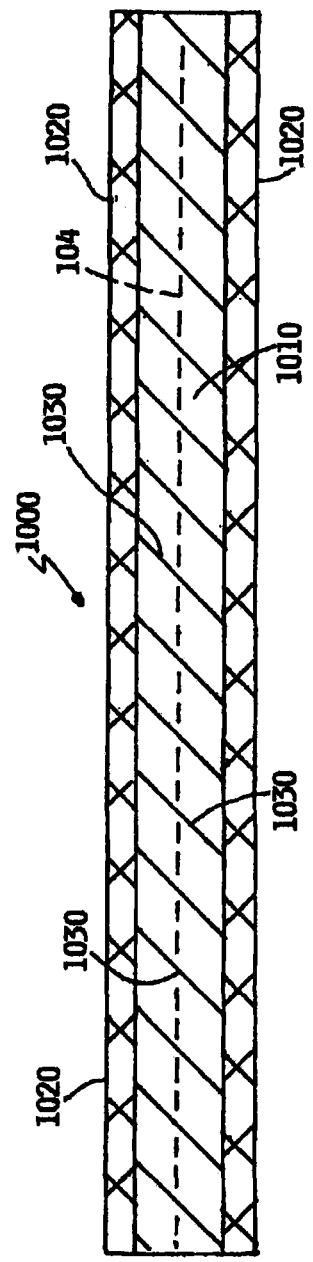
FIG. 44 is a side view of a coilable compaction device according to one embodiment.

Another embodiment of a coilable compaction device 1000 is shown in FIG. 44. The compaction device 1000 includes a spiral cut tube 1010, wherein the tube can be made of metal, for example, stainless steel; or of a shape memory alloy, for example, nitinol; or from a flexible polymer, for example, Tecothane®. The spiral cuts 1030 in the tube 1010 provide the needed flexibility to be able to flex and coil the tube 1010. Further, the spiral cuts 1030 allow for the compaction device 1000 to deform upon application of excessive compressive force by, for example, buckling, compressing, or collapsing. When the tube 1010 is extended longitudinally, the cuts of the spiral cut tube 1010 are not open or gaping, but closed, and as such, provide the longitudinal column strength in the spiral cut tube 1010 to perform the function of the compaction device 1000. The compaction device 1000 can include a polymeric hydrophilic coating, a PTFE (polytetrafluoroethylene) liner, or a silicone coating 1020 on the exterior of the tube, which can impart lubricity to the compaction device 1000. The coating 1020 can improve the movement of the compaction device 1000 through the incision or tissue puncture, and also can protect the body from a metal or alloy compaction device 1000.

In the various compaction tubes and devices described above, the compaction tube or segments of the compaction tube are described as being rigid; made of rigid material. These rigid compaction tubes or segments of compaction tubes can be made of materials such as PEEK (polyetheretherketone), ISOPLAST® (thermoplastic polyurethane resin), GRILAMID® TR55 (transparent polyamide), TROGAMID® (transparent polyamide), polyethylene, and the like.

The preceding description has been presented only to illustrate and describe example embodiments of the disclosure. It is not intended to be exhaustive or to limit the disclosure to any precise form disclosed. Many modifications and variations are possible in light of the above teachings. Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the disclosure be defined by the attached claims and their legal equivalents.

What is claimed is:

1. A compaction device for a tissue closure tool, the compaction device comprising:
   a tubular member having a first segment, a second segment, and a third segment, the first, second, and third segments being coaxially aligned, the first and second segments being tubular, the second segment being positioned between the first and third segments, the third segment being proximal to a sealing plug, the third segment having a distally-facing surface contacting a proximal end of the sealing plug, the second segment comprising a structure, the second segment being deformable along the structure when in a sealing plug tamping position and subject to application of an excessive compaction force, the structure of the second segment comprising at least one of a plurality of folds, a plurality of pleats, a lattice, or a plurality of circumscribing sections of apertures;
   wherein tamping the sealing plug distally advances the first segment toward the sealing plug.

2. The compaction device of claim 1, wherein the structure comprises thinned segment walls.

3. The compaction device of claim 2, wherein the second segment is positioned at one end of the tubular member.

4. The compaction device of claim 1, wherein the tubular member comprises a plurality of segments deformable when in a sealing plug tamping position and subject to application of an excessive compaction force.

5. The compaction device of claim 1, wherein the second segment comprises a proximal end abutting the first segment and a distal end, the distal end having a flexible shaped tip.

6. The compaction device of claim 5, wherein the second segment is rigid and the distal end of the second segment is overmolded with a flexible material.

7. A compaction device for sealing plug tamping with a tissue closure tool, the compaction device comprising:
   a first elongate member having a first end, a second end, and an inner diameter;
   a second elongate member having a first end, a second end and an outer diameter smaller than the first elongate member inner diameter, the first end of the second elongate member contacting and friction-fittingly engaged within the second end of the first elongate member, the first and second elongate members presenting columnar strength when in a sealing plug tamping position;
   wherein the first end of the second elongate member is configured to overcome the friction-fit and to slide within the first elongate member upon application of excessive compaction force to the compaction device.

8. The compaction device of claim 7, wherein the first elongate member is a tubular member, the tubular member having walls defining a central longitudinal channel, the inner diameter defining the width of the channel.

9. The compaction device of claim 8, wherein the second elongate member is a second tubular member.

10. The compaction device of claim 9, further comprising a third tubular member having a first end, a second end, and an inner diameter greater than the second tubular member outer diameter, the second end of the second tubular member friction-fittingly engageable within the first end of the third tubular member.

11. The compaction device of claim 8, wherein the second elongate member is a rack.

12. The compaction device of claim 7, wherein the first elongate member is a tubular member, the second end of the tubular member defining a chamber having side walls and an annular base, the side walls defining a diameter of the chamber, and wherein the second elongate member is a rack, the outer diameter of the rack smaller than the diameter of the chamber.

13. The compaction device of claim 12, wherein the rack first end is engageable with a spring mounted on the annular base when excessive compaction force is applied to the compaction device.

14. The compaction device of claim 7, wherein the first elongate member is a rack, the second end of the rack defining a chamber having side walls and an annular base, the side walls defining a diameter of the chamber, and wherein the second elongate member is a tubular member, the outer diameter of the tubular member is a first outer diameter at the tubular member first end, the first outer diameter smaller than the diameter of the chamber.

15. The compaction device of claim 14, wherein the second end of the tubular member comprises a second outer diameter, the second outer diameter greater than the first outer diameter and greater than the diameter of the chamber, an interface of the tubular member at the first outer diameter and the second outer diameter forming a shoulder, the second end of the rack engageable with the shoulder when excessive force is applied to the compaction device.

16. The compaction device of claim 15, wherein the first end of the tubular member further comprising a spring wound around and circumscribing at least a portion of the tubular member first end, the tubular member first end engageable within the chamber, and the second end of the rack engageable with the spring, the spring compressible when excessive force is applied to the compaction device.

17. The compaction device of claim 7, wherein the first elongate member is a rack, the second end of the rack defining a slot having side walls, the side walls defining a diameter of the slot, and wherein the second elongate member is a tubular member wherein the outer diameter of the tubular member is smaller than the diameter of the slot.

18. The compaction device of claim 7, wherein the first elongate member is a tubular member, the tubular member second end having walls defining a chamber having side walls and an annular base, a spring positioned on the annular base, the side walls defining a diameter of the chamber, and wherein the second elongate member is a second tubular member.

19. A coilable compaction device for a tissue closure tool, the compaction device comprising:
a sealing plug;
a tubular member having walls defining a central longitudinal channel, the tubular member having an inner surface and an outer surface;
a plurality of aligned coils embedded in the walls of the tubular member, each coil circumscribing the central channel, the plurality of aligned coils being positioned between the inner surface and the outer surface of the tubular member;
a stiffenable portion of the tubular member abuttingly engageable with the sealing plug, the plurality of aligned coils being configured with a column strength when a tamping force is applied to the distal end of the tubular member against the sealing plug, the plurality of aligned coils being configured to deform when an excessive force is applied to the distal end of the tubular member against the sealing plug, the excessive force exceeding the tamping force.

20. The coilable compaction device of claim 19, wherein the plurality of aligned coils is disposed in the walls of the tubular member in spaced apart groups.

21. A tissue puncture closure device comprising:
a compaction device, the compaction device comprising a tubular member having a first segment and a second segment, the first segment and the second segment coaxially aligned, the second segment deformable when in a sealing plug tamping position and subject to application of an excessive compaction force;
a sealing plug configured to be packed down by tamping using the compaction device, the sealing plug being non-destructively detachable from the compaction device, the sealing plug abutting a distal end of the compaction device without being connected to the compaction device.

22. A tissue puncture closure device comprising:
a first elongate member having a first end, a second end, an inner diameter, and an at least partially distal-facing internal neck surface;
a second elongate member having a first end, a second end and an outer diameter smaller than the first elongate member inner diameter, the first end of the second elongate member friction-fittingly engageable within the second end of the first elongate member, the second elongate member abutting the internal neck surface, the second elongate member presenting columnar strength when in a sealing plug tamping position;
a sealing plug configured to be packed down by tamping using the first and second elongate members, the sealing plug being non-destructively detachable from the first and second elongate members, the sealing plug abutting a distal end of at least one of the first and second elongate members.

23. A tissue puncture closure device comprising:
a compaction device, the compaction device comprising a coilable rack having a first end portion, a second end portion and a lumen therebetween;
a tubular member having a first end portion, a second end portion and a lumen therebetween;
a connector having a first end portion and a second end portion, the second end portion of the connector connected to the lumen in the first end portion of the coilable rack, the first end portion of the connector disposed within the lumen of the second end portion of the tubular member.

24. The tissue puncture closure device of claim 23, wherein the connector is selected from the group consisting of a spacer, a core wire, and a press-fit.

25. The tissue puncture closure device of claim 23, the connector having a central lumen, the central lumen aligned with the tubular member lumen and the coilable rack lumen, capable of accommodating a suture traveling through the coilable rack lumen and the tubular member lumen, from a proximal end of the tissue puncture closure device to a distal end of the tissue puncture closure device.

26. The tissue puncture closure device of claim 23, wherein the tubular member comprises an aperture, the aperture capable of accommodating a suture passing from the exterior of the tubular member and traveling distally through the tubular member lumen.

27. The tissue puncture closure device of claim 23, wherein the coilable rack comprises a wire coil.

28. The tissue puncture closure device of claim 23, wherein the connector is a spacer, the spacer including a recess, the recess capable of accommodating passage of a suture from an exterior of the tubular member through the recess and distally through the tubular member lumen.

29. The tissue puncture closure device of claim 23, wherein the connector is a spacer, the spacer comprising an aperture, the aperture capable of accommodating a suture from an exterior of the tubular member through the aperture and distally through the tubular member lumen.

30. A coilable compaction device comprising:
- a coilable rack having a first end portion, a second end portion and a lumen therebetween;
- a tubular member having a first end portion, a second end portion and a lumen therebetween;
- a connector having a first end portion and a second end portion, the second end portion of the connector connected to the lumen in the first end portion of the coilable rack, the first end portion of the connector disposed within the lumen of the second end portion of the tubular member.

31. A method of sealing a tissue puncture in an internal tissue wall of a patient that is accessible by a user through a percutaneous incision, the method comprising:
- exerting a tamping force on a compaction device in a distal direction to distally tamp a sealing plug toward an anchor, the distal direction extending along a longitudinal axis of the compaction device away from the user and toward the patient, the tamping force comprising an amount of excessive compaction force;
- at least partially absorbing the amount of excessive compaction force of the tamping force with the compaction device, wherein absorbing the excessive compaction force deforms the compaction device at a deformation portion of the compaction device within an insertion tube.

* * * * *